US011199776B2

(12) United States Patent
Komori et al.

(10) Patent No.: US 11,199,776 B2
(45) Date of Patent: Dec. 14, 2021

(54) RESIN COMPOSITION

(71) Applicant: TORAY INDUSTRIES, INC., Tokyo (JP)

(72) Inventors: Yusuke Komori, Otsu (JP); Kazuto Miyoshi, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 107 days.

(21) Appl. No.: 16/314,822

(22) PCT Filed: Jul. 25, 2017

(86) PCT No.: PCT/JP2017/026903
§ 371 (c)(1),
(2) Date: Jan. 2, 2019

(87) PCT Pub. No.: WO2018/021331
PCT Pub. Date: Feb. 1, 2018

(65) Prior Publication Data
US 2019/0241716 A1   Aug. 8, 2019

(30) Foreign Application Priority Data

Jul. 27, 2016 (JP) .............................. JP2016-147012

(51) Int. Cl.
G03F 7/023   (2006.01)
G03F 7/038   (2006.01)
G03F 7/40    (2006.01)
(Continued)

(52) U.S. Cl.
CPC .......... *G03F 7/0387* (2013.01); *C07C 233/43* (2013.01); *C07C 233/44* (2013.01); *C07C 233/80* (2013.01); *C07C 237/40* (2013.01); *C08G 73/106* (2013.01); *C08G 73/1007* (2013.01); *C08G 73/1039* (2013.01); *C08G 73/1046* (2013.01); *C08G 73/1067* (2013.01); *C08G 73/22* (2013.01); *C08J 5/18* (2013.01); *C08K 5/20* (2013.01); *C08L 79/08* (2013.01); *C08L 101/02* (2013.01); *G03F 7/004* (2013.01); *G03F 7/023* (2013.01); *G03F 7/0226* (2013.01); *G03F 7/038* (2013.01); *G03F 7/039* (2013.01); *G03F 7/16* (2013.01); *G03F 7/168* (2013.01); *G03F 7/20* (2013.01); *G03F 7/2004* (2013.01); *G03F 7/30* (2013.01); *G03F 7/40* (2013.01);
(Continued)

(58) Field of Classification Search
CPC ........ G03F 7/0226; G03F 7/0387; G03F 7/40; C08G 69/26
See application file for complete search history.

(56) References Cited

U.S. PATENT DOCUMENTS

| 4,507,380 A | 3/1985 | Naito et al. |
| 6,350,845 B1 | 2/2002 | Okada et al. |
| 6,958,212 B1 | 10/2005 | Hubbell et al. |
| 7,678,514 B2 * | 3/2010 | Sugiyama .......... C08G 73/1025 430/18 |

(Continued)

FOREIGN PATENT DOCUMENTS

| CN | 1165980 A | 11/1997 |
| CN | 101263180 A | 9/2008 |
| CN | 105319842 A | 2/2016 |
| EP | 0 807 852 A1 | 11/1997 |

(Continued)

OTHER PUBLICATIONS

Chemieliva Pharmaceutical Co. LTD. Reference 28999657 N,N-(4,6-dihydroxy-m-phenylene)-bis-acetamide (Year: 2000).*

(Continued)

*Primary Examiner* — John S Chu
(74) *Attorney, Agent, or Firm* — Birch, Stewart, Kolasch & Birch, LLP.

(57) ABSTRACT

The present invention provides a resin composition having a high sensitivity and serving to produce a cured film with a low water absorption rate. The resin composition includes: (a) an alkali-soluble resin and (b1) an amido-phenol compound containing a phenolic hydroxyl group in which a monovalent group as represented by the undermentioned general formula (1) is located at the ortho position and/or (b2) an aromatic amido acid compound containing a carboxy group in which a monovalent group as represented by the undermentioned general formula (2) is located at the ortho position:

[Chemical compound 1]

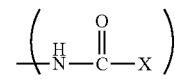

(1)

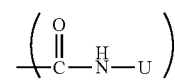

(2)

wherein in general formula (1), X is a monovalent organic group having an alkyl group that contains 2 to 20 carbon atoms and bonds directly to the carbonyl carbon in general formula (1) or a monovalent organic group that has —(YO)$_n$—; and in general formula (2), U is a monovalent organic group that has an alkyl group containing 2 to 20 carbon atoms and bonding directly to the amide nitrogen in general formula (2) or a monovalent organic group that has —(YO)$_n$—; wherein Y is an alkylene group containing 1 to 10 carbon atoms and n is an integer of 1 to 20.

9 Claims, 2 Drawing Sheets

(51) Int. Cl.
*H01L 23/29* (2006.01)
*G03F 7/20* (2006.01)
*C07C 233/80* (2006.01)
*C08G 73/10* (2006.01)
*C07C 233/44* (2006.01)
*C08G 73/22* (2006.01)
*H05B 33/10* (2006.01)
*H01L 27/32* (2006.01)
*C08L 101/02* (2006.01)
*H01L 51/50* (2006.01)
*C08L 79/08* (2006.01)
*H05B 33/22* (2006.01)
*G03F 7/004* (2006.01)
*G03F 7/022* (2006.01)
*C08K 5/20* (2006.01)
*C07C 233/43* (2006.01)
*C07C 237/40* (2006.01)
*C08J 5/18* (2006.01)
*G03F 7/039* (2006.01)
*G03F 7/16* (2006.01)
*G03F 7/30* (2006.01)
*H01L 21/78* (2006.01)
*H01L 23/544* (2006.01)
*H01L 23/00* (2006.01)
*H01L 27/12* (2006.01)
*H01L 51/00* (2006.01)
*H01L 51/56* (2006.01)

(52) U.S. Cl.
CPC ............ *H01L 21/78* (2013.01); *H01L 23/293* (2013.01); *H01L 23/544* (2013.01); *H01L 24/03* (2013.01); *H01L 24/05* (2013.01); *H01L 24/13* (2013.01); *H01L 27/1248* (2013.01); *H01L 27/32* (2013.01); *H01L 27/3258* (2013.01); *H01L 51/0018* (2013.01); *H01L 51/0035* (2013.01); *H01L 51/50* (2013.01); *H01L 51/56* (2013.01); *H05B 33/10* (2013.01); *H05B 33/22* (2013.01); *C08J 2379/08* (2013.01); *H01L 2223/5446* (2013.01); *H01L 2224/024* (2013.01); *H01L 2224/02331* (2013.01); *H01L 2224/0362* (2013.01); *H01L 2224/13024* (2013.01)

(56) References Cited

U.S. PATENT DOCUMENTS

| | | | |
|---|---|---|---|
| 8,269,358 | B2 | 9/2012 | Terakawa |
| 9,575,410 | B2 * | 2/2017 | Shibui ................... G03F 7/023 |
| 2010/0044888 | A1 * | 2/2010 | Terakawa ........... C08G 73/1025 257/788 |
| 2014/0349222 | A1 | 11/2014 | Shibui et al. |
| 2017/0102613 | A1 * | 4/2017 | Shibui .................. G03F 7/0226 |

FOREIGN PATENT DOCUMENTS

| | | | |
|---|---|---|---|
| JP | 57-207250 | A | 12/1982 |
| JP | 59-36255 | A | 2/1984 |
| JP | 62-5238 | A | 1/1987 |
| JP | 1-145657 | A | 6/1989 |
| JP | 6-110150 | A | 4/1994 |
| JP | 8-171184 | A | 7/1996 |
| JP | 2000-131845 | A | 5/2000 |
| JP | 2001-11177 | A | 1/2001 |
| JP | 2001-183835 | A | 7/2001 |
| JP | 2002-528632 | A | 9/2002 |
| JP | 2002-535108 | A | 10/2002 |
| JP | 2009-79028 | A | 4/2009 |
| JP | 2009079028 | A * | 4/2009 |
| JP | 2010215594 | A * | 9/2010 |
| JP | 2010-266530 | A | 11/2010 |
| JP | 2013-3310 | A | 1/2013 |
| KR | 10-1398293 | B1 | 5/2014 |
| TW | 201329622 | A1 | 7/2013 |
| WO | WO 00/26319 | A1 | 5/2000 |
| WO | WO 2012/052562 | A1 | 4/2012 |

OTHER PUBLICATIONS

Chemspider online structure search (Year: 2000).*
https://www.chemexper.com/searchResult.shtml?searchTemplate=mol.value%3D%3F+elsor+mol.value%3D%7E%3F&searchValue=C1%28NC%28C%29%3DO%29%3DCC%28NC%28C%29%3DO%29%3DC%28O%29C%3DC1O&format=ccd2013%2Cccd&target=structure&options=brandqtyoffercrm&i=35953b&country=US&sort=%3Eentry.counter.*
Chemspider online structure search: http://www.chemspider.com/Chemical-Structure.68641050.html?rid=55c6c105-fb53-4cdb-9fd6-485cd959724b.*
International Search Report and Written Opinion of the International Searching Authority (Forms PCT/ISA/210, PCT/ISA/220 and PCT/ISA/237) for International Application No. PCT/JP2017/026903, dated Sep. 19, 2017.
Krishnan et al., "Influence of Molecular Weight on Molecular Ordering and Proton Transport in Organized Sulfonated Polyimide Thin Films," The Journal of Physical Chemistry, vol. 119, Sep. 2, 2015, p. 21767-21774.
English translation of Chinese Office Action for Chinese Application No. 201780045579.5, dated Aug. 20, 2021.
Yue et al., "Practical Technology Guide of Photosensitive Materials and Plate", Printing Industry Press, Mar. 2007, pp. 1-5, with partial translation.

* cited by examiner

RESIN COMPOSITION

TECHNICAL FIELD

The present invention relates to a resin composition including an alkali-soluble resin and an amido-phenol compound.

BACKGROUND ART

Since heat resistant resins such as polyimide and polybenzoxazole have excellent heat resistance and electric insulation properties, photosensitive resin compositions containing these heat resistant resins have been used as surface protection layers and interlaminar insulation layers of semiconductor devices such as LSI, insulation layers of organic electroluminescent devices and organic EL display devices, and planarization layers of TFT substrates for display devices, and the like.

There are increasing demands for semiconductors with high reliability, particularly in high temperature and high humidity environments, resulting in necessity of resin compositions with low water absorptivity as materials for surface protection layers and interlaminar insulation layers of semiconductors. Regarding organic EL display apparatuses, as well, there are increasing demands for resin compositions with low water absorptivity as materials for insulation layers of organic EL displaying apparatuses because organic EL luminescence materials are liable to degradation caused by moisture. In recent years, furthermore, demands are also increasing for photosensitive resin compositions with higher sensitivity that realize shortened exposure periods to permit the application of larger substrates and the improvement in productivity. Against such a background, there is a strong call for the development of a photosensitive resin composition that permits high sensitivity patterning and the production of cured film with low water absorptivity.

To realize this, there is a proposal for a positive photosensitive resin composition that incorporates an alkali-soluble resin, a diazonaphthoquinone compound, and a phenolic hydroxyl group-free and methylol group-containing compound because such a positive photosensitive resin composition can serve to produce a cured film with low water absorptivity (see, for example, Patent document 1). However, this photosensitive resin composition has the problem of poor sensitivity. To eliminate this problem, there are proposals of photosensitive resin compositions with high sensitivity and high resolution such as, for example, a positive photosensitive resin composition containing a polyamide resin, a photosensitive quinone diazide compound, and an amido-phenol compound as essential components (see, for example, Patent document 2) and a positive photosensitive resin composition containing an alkali-soluble resin, a photosensitive diazoquinone compound, and a phenol compound (see, for example, Patent document 3).

PRIOR ART DOCUMENTS

Patent Documents

[Patent document 1]
U.S. Unexamined Patent Application Publication No. 2004-259020
[Patent document 2]
Japanese Unexamined Patent Publication (Kokai) No. 2001-183835

[Patent document 3]
Japanese Unexamined Patent Publication (Kokai) No. 2004-125815

SUMMARY OF THE INVENTION

Problems to be Solved by the Invention

When using such a photosensitive resin composition as described in Patent document 2 or 3, however, the phenolic hydroxyl group, which is a polar group, tends to remain in the cured film, possibly leading to the problem of a high water absorption rate. Thus, an object of the present invention is to provide a high sensitivity resin composition that serves to produce a cured film with a low water absorption rate.

Means of Solving the Problems

The present invention relates to a resin composition including (a) an alkali-soluble resin and (b1) an amido-phenol compound containing a phenolic hydroxyl group in which a monovalent group as represented by the undermentioned general formula (1) is located at the ortho position and/or (b2) an aromatic amido acid compound containing a carboxy group in which a monovalent group as represented by the undermentioned general formula (2) is located at the ortho position.

[Chemical compound 1]

(In general formula (1), X is a monovalent organic group that has an alkyl group containing 2 to 20 carbon atoms and bonding directly to the carbonyl carbon in general formula (1) or a monovalent organic group that has —(YO)$_n$—. In general formula (2), U is a monovalent organic group that has an alkyl group containing 2 to 20 carbon atoms and bonding directly to the amide nitrogen in general formula (2) or a monovalent organic group that has —(YO)$_n$—. Y is an alkylene group containing 1 to 10 carbon atoms, and n is an integer of 1 to 20.)

Advantageous Effect of the Invention

The resin composition according to the present invention has high sensitivity, and the use of the resin composition according to the present invention permits the production of a cured film with a low water absorption rate.

DESCRIPTION OF PREFERRED EMBODIMENTS

Figure 1:
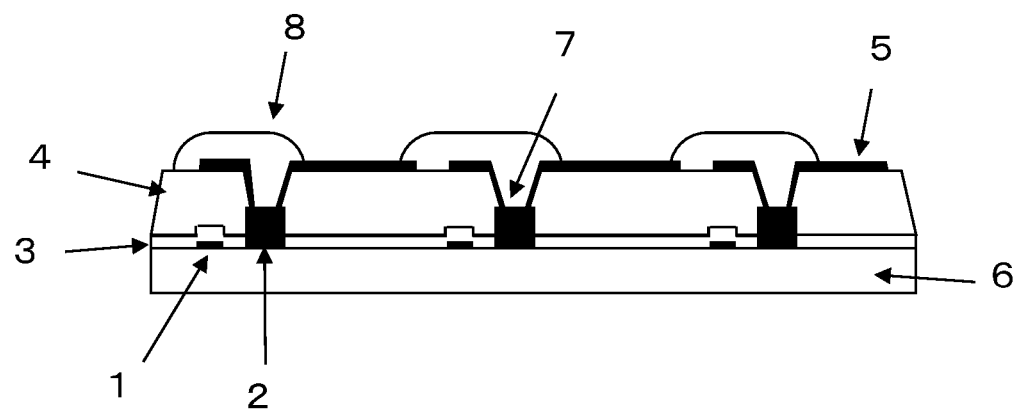
FIG. 1 is a cross-sectional view of a typical TFT substrate.

An embodiment of the present invention is described in detail below.

<Alkali-Soluble Resin (a)>

The resin composition according to the present invention contains an alkali-soluble resin (a). The incorporation of an alkali-soluble resin (a) serves to prepare a resin composition with patternability. For the present invention, alkali-solubility test is performed by dissolving a resin sample in γ-butyrolactone to prepare a solution, spreading it over a silicon wafer, prebaking it at 120° C. for 4 minutes to form a prebaked film with a film thickness of 10 μm±0.5 μm, immersing the prebaked film in an aqueous solution containing 2.38 wt. % of tetramethyl ammonium hydroxide at 23±1° C. for 1 minute, rinsing it with pure water, and determining the dissolution rate from the decrease in film thickness, and the resin is judged to be alkali-soluble if the rate is 50 nm/min or more.

The alkali-soluble resin (a) used for the present invention preferably has an acidic group in the structural unit and/or at a backbone chain end of the resin to impart alkali-solubility. Examples of the acidic group include carboxy groups, phenolic hydroxyl groups, and sulfonic acid groups. It is preferable furthermore for the alkali-soluble resin (a) to have a fluorine atom to show water repellency.

Specific examples of the alkali-soluble resin (a) include, but not limited to, polyimide, polyimide precursors, polybenzoxazole, polybenzoxazole precursors, polyamide-imide, polyamide-imide precursors, polyamide, polymers obtainable from radical-polymerizable monomers having alkali-soluble groups, and phenol resin. Two or more of these resins may be contained together. Of these alkali-soluble resins, polyimide, polybenzoxazole, polyamide-imide, precursors thereof and/or copolymers thereof are preferable because of high heat resistance and smaller outgassing at high temperatures; polyimide, polyimide precursors, polybenzoxazole precursors and copolymers thereof are more preferable; and polyimide precursors and polybenzoxazole precursors are still more preferable from the viewpoint of ensuring further improved sensitivity. Here, a polyimide precursor is a resin that can be converted into polyimide through heat treatment, chemical treatment, etc., and examples thereof include polyamic acid and polyamic acid ester. Here, a polybenzoxazole precursor is a resin that can be converted into polybenzoxazole through heat treatment, chemical treatment, etc., and examples thereof include polyhydroxyamide.

A polyimide compound as described above has a structural unit as represented by general formula (17) given below, whereas a polyimide precursor and a polybenzoxazole precursor have a structural unit as represented by general formula (18) given below. Two or more of these may be contained and a copolymer resin of a structural unit represented by general formula (17) and a structural unit represented by general formula (18) may be used.

[Chemical compound 2]

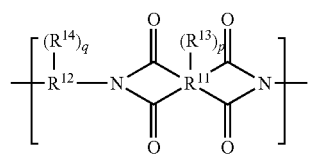
(17)

In general formula (17), $R^{11}$ is a tetravalent to decavalent organic group, and $R^{12}$ is a divalent to octavalent organic group. $R^{13}$ and $R^{14}$ are each a carboxy group, a sulfonic acid group, or a phenolic hydroxyl group. The p $R^{13}$ groups and the q $R^{14}$ groups may be identical with or different from each other. Furthermore, p and q are each an integer of 0 to 6.

[Chemical compound 3]

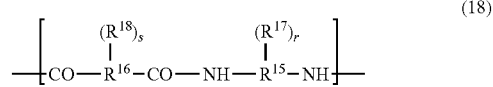
(18)

(In general formula (18), $R^{15}$ and $R^{16}$ independently denote a divalent to octavalent organic groups. $R^{17}$ and $R^{18}$ each denote a phenolic hydroxyl group, sulfonic acid group, or $COOR^{19}$, and each plurality of groups may be identical with or different from each other. $R^{19}$ denotes a hydrogen atom or a monovalent hydrocarbon group containing 1 to 20 carbon atoms. Furthermore, r and s are each an integer of 0 to 6. Here, the relation of r+s>0 holds.

The aforementioned polyimide, polyimide precursors, polybenzoxazole precursors, and copolymers thereof preferably contain 5 to 100,000 structural units that are represented by general formula (17) or (18). They may contain another structural unit in addition to the structural units that are represented by general formula (17) or (18). In this case, it is preferable for the structural units that are represented by general formula (17) or (18) to account for 50 mol % or more of the total number of structural units.

In general formula (17) given above, $R^{11}$-$(R^{13})^p$ represents an dianhydride residue. $R^{11}$ is a tetravalent to decavalent organic group and in particular, it is preferably an organic group containing 5 to 40 carbon atoms and having an aromatic ring or a cycloaliphatic group.

Specific examples of the dianhydride include pyromellitic dianhydride, 3,3',4,4'-biphenyl tetracarboxylic dianhydride, 2,3,3',4'-biphenyl tetracarboxylic dianhydride, 2,2',3,3'-biphenyl tetracarboxylic dianhydride, 3,3',4,4'-benzophenone tetracarboxylic dianhydride, 2,2',3,3'-benzophenone tetracarboxylic dianhydride, 2,2-bis(3,4-dicarboxyphenyl) propane dianhydride, 2,2-bis(2,3-dicarboxyphenyl) propane dianhydride, 1,1-bis(3,4-dicarboxyphenyl) ethane dianhydride, 1,1-bis(2,3-dicarboxyphenyl) ethane dianhydride, bis(3,4-dicarboxyphenyl) methane dianhydride, bis(2,3-dicarboxyphenyl) methane dianhydride, bis(3,4-dicarboxyphenyl) ether dianhydride, 1,2,5,6-naphthalene tetracarboxylic dianhydride, 9,9-bis(3,4-dicarboxyphenyl) fluorene dianhydride, 9,9-bis{4-(3,4-dicarboxyphenoxy)phenyl} fluorene dianhydride, 2,3,6,7-naphthalene tetracarboxylic dianhydride, 2,3,5,6-pyridine tetracarboxylic dianhydride, 3,4,9,10-perylene tetracarboxylic dianhydride, and 2,2-bis(3,4-dicarboxyphenyl) hexafluoropropane dianhydride, as well as aromatic tetracarboxylic dianhydrides such as those dianhydrides having structures as shown below, aliphatic tetracarboxylic dianhydrides such as butane tetracarboxylic dianhydride, and aliphatic tetracarboxylic dianhydrides having cycloaliphatic groups such as 1,2,3,4-cyclopentane tetracarboxylic dianhydride. Two or more of these may be used in combination.

[Chemical compound 4]

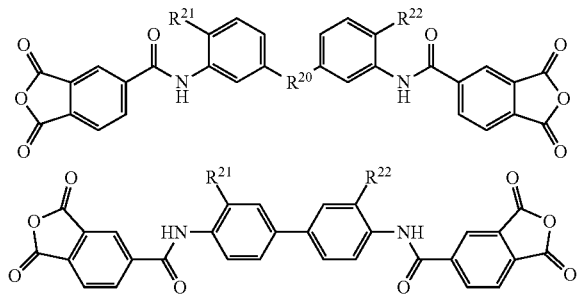

$R^{20}$ denotes an oxygen atom, $C(CF_3)_2$, or $C(CH_3)_2$. $R^{21}$ and $R^{22}$ are each a hydrogen atom or a hydroxyl group.

In general formula (18) given above, $R^{16}\text{-}(R^{18})_s$, represents an acid residue. $R^{16}$ is a divalent to octavalent organic group and in particular, it is preferably an organic group containing 5 to 40 carbon atoms and having an aromatic ring or a cycloaliphatic group.

Examples of the acid components include dicarboxylic acids such as terephthalic acid, isophthalic acid, diphenyl ether dicarboxylic acid, bis(carboxyphenyl) hexafluoropropane, biphenyl dicarboxylic acid, benzophenone dicarboxylic acid, and triphenyl dicarboxylic acid; tricarboxylic acids such as trimellitic acid, trimesic acid, diphenyl ether tricarboxylic acid, and biphenyl tricarboxylic acid; and tetracarboxylic acids including aromatic tetracarboxylic acids such as pyromellitic acid, 3,3',4,4'-biphenyl tetracarboxylic acid, 2,3,3',4'-biphenyl tetracarboxylic acid, 2,2',3,3'-biphenyl tetracarboxylic acid, 3,3',4,4'-benzophenone tetracarboxylic acid, 2,2',3,3'-benzophenone tetracarboxylic acid, 2,2-bis(3,4-dicarboxyphenyl) hexafluoropropane, 2,2-bis(2,3-dicarboxyphenyl) hexafluoropropane, 1,1-bis(3,4-dicarboxyphenyl) ethane, 1,1-bis(2,3-dicarboxyphenyl) ethane, bis(3,4-dicarboxyphenyl) methane, bis(2,3-dicarboxyphenyl) methane, bis(3,4-dicarboxyphenyl) ether, 1,2,5,6-naphthalene tetracarboxylic acid, 2,3,6,7-naphthalene tetracarboxylic acid, 2,3,5,6-pyridine tetracarboxylic acid, 3,4,9,10-perylene tetracarboxylic acid, and others having structures as shown below; aliphatic tetracarboxylic acids such as butane tetracarboxylic acid; and aliphatic tetracarboxylic acids having cycloaliphatic groups such as 1,2,3,4-cyclopentane tetracarboxylic acid. Two or more of these may be used in combination.

[Chemical compound 5]

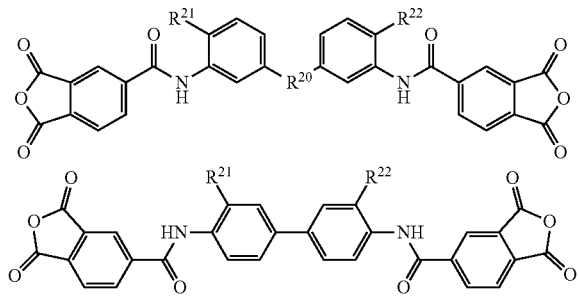

$R^{20}$ denotes an oxygen atom, $C(CF_3)_2$, or $C(CH_3)_2$. $R^{21}$ and $R^{22}$ are each a hydrogen atom or a hydroxyl group.

In the case of tricarboxylic acids and tetracarboxylic acids, in particular, one or two carboxy groups correspond to the $R^{18}$ group in general formula (18). In the dicarboxylic acids, tricarboxylic acids, and tetracarboxylic acids given above, hydrogen atoms may be substituted by $R^{18}$ groups in general formula (18). It is more preferable that 1 to 4 of the $R^{18}$ groups are substituted by hydroxyl groups. Each of these acids may be used in its original form or in the form of an anhydride or an active ester.

$R^{12}\text{-}(R^{14})_q$ in general formula (17) given above and $R^{15}\text{-}(R^{17})_r$ in general formula (18) given above each represent a diamine residue. $R^{12}$ and $R^{15}$ are each a divalent to octavalent organic group and in particular, it is preferably an organic group containing 5 to 40 carbon atoms and having an aromatic ring or a cycloaliphatic group.

Specific examples of the diamine include aromatic diamines such as 3,4'-diaminodiphenyl ether, 4,4'-diaminodiphenyl ether, 3,4'-diaminodiphenyl methane, 4,4'-diaminodiphenyl methane, 1,4-bis(4-aminophenoxy) benzene, benzidine, m-phenylene diamine, p-phenylene diamine, 1,5-naphthalene diamine, 2,6-naphthalene diamine, bis(4-aminophenoxy) biphenyl, bis{4-(4-aminophenoxy) phenyl} ether, 1,4-bis(4-aminophenoxy) benzene, 2,2'-dimethyl-4,4'-diaminobiphenyl, 2,2'-diethyl-4,4'-diaminobiphenyl, 3,3'-dimethyl-4,4'-diaminobiphenyl, 3,3'-diethyl-4,4'-diaminobiphenyl, 2,2',3,3'-tetramethyl-4,4'-diaminobiphenyl, 3,3',4,4'-tetramethyl-4,4'-diaminobiphenyl, 2,2'-di(trifluoromethyl)-4,4'-diaminobiphenyl, and 9,9-bis(4-aminophenyl) fluorine; 2,2'-bis(trifluoromethyl)-5,5'-dihydroxy benzidine, and compounds listed above in which at least some of the hydrogen atoms in the aromatic rings are substituted by alkyl groups or halogen atoms; aliphatic diamines having cycloaliphatic groups such as cyclohexyl diamine and methylene biscyclohexyl amine, and diamines having structures as shown below. Two or more of these may be used in combination.

[Chemical compound 6]

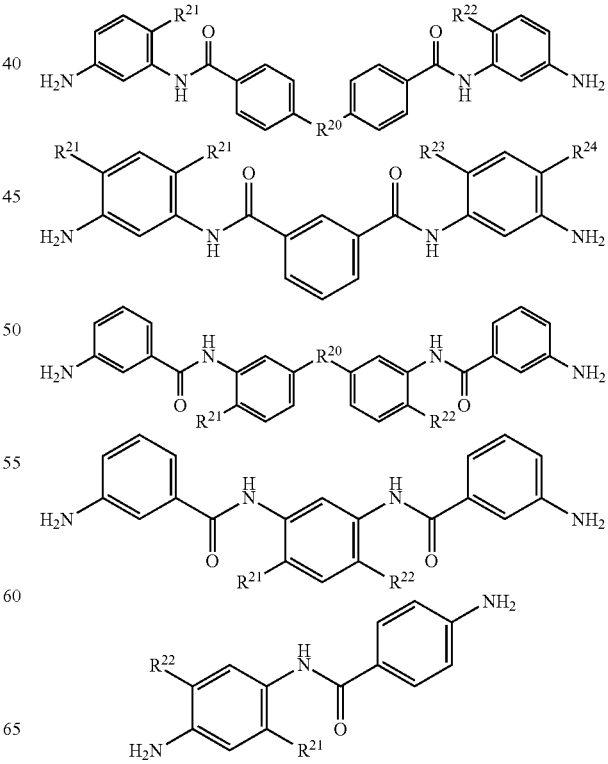

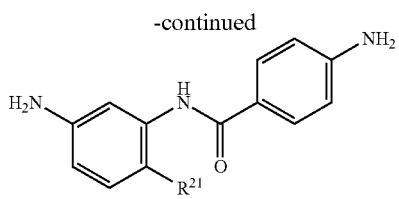

$R^{20}$ denotes an oxygen atom, $C(CF_3)_2$, or $C(CH_3)_2$. $R^{21}$ to $R^{24}$ are each a hydrogen atom or a hydroxyl group.

Each of these diamines may be used in its original form or in the form of a corresponding diisocyanate compound or trimethylsilylated diamine.

Chain ends of such a resin may be capped with an acidic group-containing monoamine, anhydride, acid chloride, monocarboxylic acid, active ester compound, or any other end-capping agent to provide a resin having acidic groups at backbone chain ends.

Preferable examples of monoamines containing acidic groups include 5-amino-8-hydroxyquinoline, 1-hydroxy-7-aminonaphthalene, 1-hydroxy-6-aminonaphthalene, 1-hydroxy-5-aminonaphthalene, 1-hydroxy-4-aminonaphthalene, 2-hydroxy-7-aminonaphthalene, 2-hydroxy-6-aminonaphthalene, 2-hydroxy-5-aminonaphthalene, 1-carboxy-7-aminonaphthalene, 1-carboxy-6-aminonaphthalene, 1-carboxy-5-aminonaphthalene, 2-carboxy-7-aminonaphthalene, 2-carboxy-6-aminonaphthalene, 2-carboxy-5-aminonaphthalene, 2-aminobenzoic acid, 3-aminobenzoic acid, 4-aminobenzoic acid, 4-aminosalicylic acid, 5-aminosalicylic acid, 6-aminosalicylic acid, 3-amino-4,6-dihydroxy pyrimidine, 2-aminophenol, 3-aminophenol, 4-aminophenol, 2-aminothiophenol, 3-aminothiophenol, and 4-aminothiophenol. Two or more of these may be used in combination.

Preferable examples of the anhydride include phthalic anhydride, maleic anhydride, nadic anhydride, cyclohexane dicarboxylic anhydride, and 3-hydroxyphthalic anhydride. Two or more of these may be used in combination.

Preferable examples of the monocarboxylic acid include 3-carboxyphenol, 4-carboxyphenol, 3-carboxythiophenol, 4-carboxythiophenol, 1-hydroxy-7-carboxynaphthalene, 1-hydroxy-6-carboxynaphthalene, 1-hydroxy-5-carboxynaphthalene, 1-mercapto-7-carboxynaphthalene, 1-mercapto-6-carboxynaphthalene, and 1-mercapto-5-carboxynaphthalene. Two or more of these may be used in combination.

Preferable examples of the acid chloride include monoacid chloride compounds in the form of the above monocarboxylic acids with the carboxy group converted into acid chloride and monoacid chloride compounds in the form of dicarboxylic acids with only one carboxy group converted into acid chloride such as terephthalic acid, phthalic acid, maleic acid, cyclohexane dicarboxylic acid, 1,5-dicarboxynaphthalene, 1,6-dicarboxynaphthalene, 1,7-dicarboxynaphthalene, and 2,6-dicarboxynaphthalene. Two or more of these may be used in combination.

Preferable examples of the active ester compound include reaction products between the aforementioned monoacid chloride compounds and N-hydroxybenzotriazole, N-hydroxy-5-norbornene-2,3-dicarboxyimide, etc. Two or more of these may be used in combination.

End capping agents introduced in a resin can be detected easily by methods as described below. A resin containing an end capping agent may be dissolved in, for instance, an acid solution to decompose it into the amine components and acid components, that is, the constituent units of the resin, and then the end capping agent can be detected easily from observations made by gas chromatography (GC) or NMR spectroscopy. In another method, detection can be carried out by subjecting a resin specimen containing an end capping agent directly to pyrolysis gas chromatograph (PGC), infrared spectroscopy, or $^{13}$C-NMR spectroscopy.

The alkali-soluble resin (a) used for the present invention can be synthesized by a generally known method.

To produce a polyamic acid or polyamic ester to use as a polyimide precursor, available methods include, for example, a method in which a tetracarboxylic dianhydride and a diamine compound is reacted at a low temperature, a method in which a diester is produced from a tetracarboxylic dianhydride and an alcohol and then reacted with an amine in the presence of a condensation agent, and a method in which a diester is produced from a tetracarboxylic dianhydride and an alcohol and the remaining dicarboxylic acid is converted into an acid chloride, which is then reacted with an amine.

To produce a polyhydroxyamide to use as a polybenzoxazole precursor, it can be achieved by, for example, subjecting a bisaminophenol compound and a dicarboxylic acid to condensation reaction. Specifically, available methods include, for example, a method in which an acid is reacted with a dehydration condensation agent such as dicyclohexyl carbodiimide (DCC), followed by adding a bisaminophenol compound, and a method in which a tertiary amine such as pyridine is added to a solution of a bisaminophenol compound, followed by dropping a solution of dicarboxylic dichloride.

Available methods to produce a polyimide include, for example, a method in which a polyamic acid or a polyamic acid ester produced as described above is subjected to dehydration cyclization. Available methods for the dehydration cyclization include chemical treatment with an acid or a base and heat treatment.

Available methods to produce a polybenzoxazole include, for example, a method in which a polyhydroxyamide produced as described above is subjected to dehydration cyclization. Available methods for the dehydration cyclization include chemical treatment with an acid or a base and heat treatment.

Useful polyamide-imide precursors include polymers through reaction between a tricarboxylic acid, corresponding tricarboxylic anhydride, tricarboxylic anhydride halide, etc., and a diamine compound, and in particular it is preferable to use a polymer formed from a trimellitic anhydride chloride and an aromatic diamine compound. Available methods for the production of a polyamide-imide precursor include, for example, a method in which a tricarboxylic acid, a corresponding tricarboxylic anhydride, tricarboxylic anhydride halide, etc., is reacted with a diamine compound at a low temperature.

Available methods for the production of a polyamide-imide include, for example, a method in which a trimellitic anhydride is reacted with an aromatic diisocyanate and a method in which a polyamide-imide precursor produced by the aforementioned procedure is subjected to dehydration cyclization. Available methods for the dehydration cyclization include chemical treatment with an acid or a base and heat treatment.

The polymer to use that is produced from a radical polymerizable monomer having an alkali-soluble group is preferably a polymer produced from a radical polymerizable monomer having a phenolic hydroxyl group or a carboxy group to serve for developing alkali-solubility. It may be a copolymer produced from a radical polymerizable monomer as described above and other radical polymerizable monomer. Preferable examples of the radical polymerizable monomer having a phenolic hydroxyl group or a carboxy group include o-hydroxystyrene, m-hydroxystyrene, and p-hydroxystyrene, which may be substituted by an alkyl or alkoxy group. Preferable examples of such other radical polymerizable monomer include esterification products of styrene, substituted products thereof, butadiene, isoprene, methacrylic acid, or acrylic acid.

Preferable examples of the phenol resin include novolac phenol resins and resol phenol resins.

<Amido-Phenol Compound (b1) and Aromatic Amido Acid Compound (b2)>

The resin composition according to the present invention includes an amido-phenol compound containing a phenolic hydroxyl group in which a monovalent group as represented by the undermentioned general formula (1) is located at the ortho position (hereinafter, occasionally referred to simply as amido-phenol compound (b1)) and/or an aromatic amido acid compound containing a carboxy group in which a monovalent group as represented by the undermentioned general formula (2) is located at the ortho position (hereinafter, occasionally referred to simply as aromatic amido acid compound (b2)). The amido-phenol compound (b1) has a phenolic hydroxyl group and the aromatic amido acid compound (b2) has a carboxy group. In the case of, for example, a positive photosensitive resin composition, therefore, the phenolic hydroxyl group or the carboxy group works to accelerate the dissolution of the light-exposed regions in the development step, thereby ensuring a higher sensitivity. On the other hand, the amido-phenol compound (b1) contains a phenolic hydroxyl group in which an amido group is located at the ortho position and the aromatic amido acid compound (b2) contains a carboxy group in which an amido group is located at the ortho position. Therefore, as a result of cyclodehydration reaction, the phenolic hydroxyl group and the carboxy groups, which are polar groups, will not remain after the curing step, making it possible to produce a cured film with a low water absorptivity. From the viewpoint of ensuring a further improved solubility in alkaline developers and a further improved sensitivity, it is preferable for the amido-phenol compound (b1) and the aromatic amido acid compound (b2) to have two or more monovalent groups that are represented by the undermentioned general formula (1) or (2).

[Chemical compound 7]

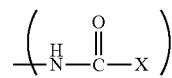
(1)

In general formula (1), X is a monovalent organic group that has an alkyl group containing 2 to 20 carbon atoms and bonding directly to the carbonyl carbon in general formula (1) or a monovalent organic group that has $-(YO)_n-$. Y is an alkylene group containing 1 to 10 carbon atoms, and n is an integer of 1 to 20.

If X has $-(YO)_n-$ or an alkyl group containing 2 to 20 carbon atoms and bonding directly to the carbonyl carbon in general formula (1), the dehydration cyclization rate will be high at or below 250° C. to ensure a lower water absorption rate after the curing step. When X is an alkyl group, it preferably contains 10 or less, more preferably 6 or less, carbon atoms from the viewpoint of ensuring an improved heat resistance. In the case where X is a monovalent organic group containing $-(YO)_n-$, Y is preferably a methylene group, an ethylene group, a propylene group, or a butylene group from the viewpoint of ensuring an improved heat resistance. In the case where Y is a methylene group, n is preferably 2 or more from the viewpoint of ensuring an improved dehydration cyclization rate. It is more preferably 3 or more. From the viewpoint of ensuring an improved heat resistance, on the other hand, n is preferably 10 or less. In the case where Y is not a methylene group, n is preferably 2 to 10 from the viewpoint of ensuring an improved heat resistance. From the viewpoint of ensuring an improved heat resistance, furthermore, X may contain any appropriate substituent group and, for example, preferably has an aryl group at a chain end.

[Chemical compound 8]

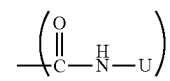
(2)

In general formula (2), U is a monovalent organic group that has an alkyl group containing 2 to 20 carbon atoms and bonding directly to the amide nitrogen in general formula (2) or a monovalent organic group that has $-(YO)_n-$. Y is an alkylene group containing 1 to 10 carbon atoms, and n is an integer of 1 to 20.

If U has $-(YO)_n-$ or an alkyl group containing 2 to 20 carbon atoms and bonding directly to the amide nitrogen in general formula (2), the dehydration cyclization rate will be high at or below 250° C. to ensure a lower water absorption rate after the curing step. When U is an alkyl group, it preferably contains 10 or less, more preferably 6 or less, carbon atoms from the viewpoint of ensuring an improved heat resistance. In the case where U is a monovalent organic group containing $-(YO)_n-$, Y is preferably a methylene group, an ethylene group, a propylene group, or a butylene group from the viewpoint of ensuring an improved heat resistance. In the case where Y is a methylene group, n is preferably 2 or more from the viewpoint of ensuring an improved dehydration cyclization rate. It is more preferably 3 or more. From the viewpoint of ensuring an improved heat resistance, on the other hand, n is preferably 10 or less. In the case where Y is not a methylene group, n is preferably 2 to 10 from the viewpoint of ensuring an improved heat resistance. From the viewpoint of ensuring an improved heat resistance, furthermore, U may contain any appropriate substituent group and, for example, preferably has an aryl group at a chain end.

X in general formula (1) and U in general formula (2) are each an alkyl group containing 2 to 20 carbon atoms and good examples thereof include ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and icosyl. Yin general formula (1) and general formula (2) is an alkylene group containing 1 to 10 carbon atoms and good examples include methylene, ethylene, propylene, butylene, pentylene, hexylene, heptylene, octylene, and decylene.

Examples of the amido-phenol compound (b1) used for the present invention include compounds represented by any one of the undermentioned general formulae (3) to (5). Such compounds may also be used as dissolution accelerators.

[Chemical compound 9]

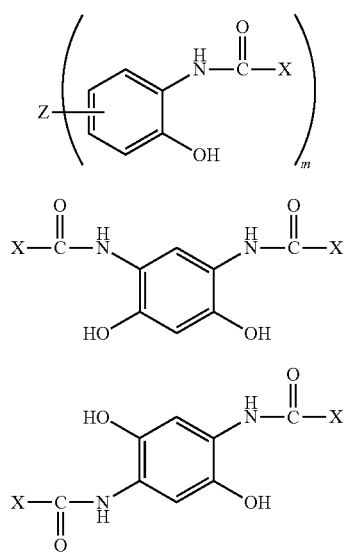

In general formulae (3) to (5), m is an integer of 1 to 4. X is a monovalent organic group that has an alkyl group containing 2 to 20 carbon atoms and bonding directly to the carbonyl carbon in general formulae (3) to (5) or a monovalent organic group that has —(YO)$_n$—. Y is an alkylene group containing 1 to 10 carbon atoms, and n is an integer of 1 to 20.

When X is an alkyl group, it preferably contains 10 or less, more preferably 6 or less, carbon atoms. In the case where X is a monovalent organic group containing —(YO)$_n$—, Y is preferably a methylene group, an ethylene group, a propylene group, or a butylene group. In the case where Y is a methylene group, n is preferably 2 or more, more preferably 3 or more. It is also preferably 10 or less. In the case where Y is not a methylene group, n is preferably 2 to 10. Furthermore, X may contain any appropriate substituent group and, for example, preferably has an aryl group at a chain end.

In general formulae (3) to (5), Z is a single bond, a hydrogen atom, an alkoxy group, —O—, —SO$_2$—, —C(CF$_3$)$_2$—, —O—R$^1$—O—, —C(=O)—, —C(=O)O—R$^2$—OC(=O)—, —C(=O)NH—R$^3$—NHC(=O)—, or a monovalent to tetravalent hydrocarbon group containing 1 to 20 carbon atoms. R$^1$ to R$^3$ are each a divalent hydrocarbon group containing 1 to 20 carbon atoms. From the viewpoint of ensuring an improved solubility, the hydrocarbon group more preferably contains 1 to 10 carbon atoms. The hydrocarbon group may be either saturated or unsaturated. When Z is a single bond, however, m should be 2.

An amido-phenol compound (b1) to use for the present invention can be prepared by reacting a compound containing a phenolic hydroxyl group in which an amino group is located at the ortho position or a hydrochloride thereof with a corresponding acid chloride. Examples of the compound containing a phenolic hydroxyl group in which an amino group is located at the ortho position include diamines containing hydroxyl groups such as 2-aminophenol, 2,4-dihydroxy-m-phenylene diamine, 2,5-dihydroxy-p-phenylene diamine, 4,6-diaminoresorcinol, 3,3'-diamino-4,4'-dihydroxydiphenyl, 4,4'-diamino-3,3'-dihydroxydiphenyl, 3,4'-diamino-3',4-dihydroxydiphenyl, 3,3'-diamino-4,4'-dihydroxydiphenyl ether, 4,4'-diamino-3,3'-dihydroxydiphenyl ether, 3,4'-diamino-3',4-dihydroxydiphenyl ether, 3,3'-diamino-4,4'-dihydroxydiphenyl hexafluoropropane, 4,4'-diamino-3,3'-dihydroxydiphenyl hexafluoropropane, 3,4'-diamino-3',4-dihydroxydiphenyl hexafluoropropane, 3,3'-diamino-4,4'-dihydroxy benzophenone, 4,4'-diamino-3,3'-dihydroxy benzophenone, 3,4'-diamino-3',4-dihydroxy benzophenone, 3,3'-diamino-4,4'-dihydroxydiphenyl sulfone, 4,4'-diamino-3,3'-dihydroxydiphenyl sulfone, 3,4'-diamino-3',4-dihydroxydiphenyl sulfone, bis(3-amino-4-hydroxyphenyl) propane, bis(3-amino-4-hydroxyphenyl) methylene, bis(3-amino-4-hydroxyphenyl) fluorene, and 2,2'-bis(trifluoromethyl)-5,5'-dihydroxy benzidine, in which some of the hydrogen atoms in the aromatic rings may be substituted by an alkyl group containing 1 to 10 carbon atoms, a fluoroalkyl group, or a halogen atom.

Examples of the acid chloride include acid chlorides such as propanoyl chloride, butanoyl chloride, pentanoyl chloride, hexanoyl chloride, heptanoyl chloride, octanoyl chloride, nonanoyl chloride, decanoyl chloride, and lauroyl chloride, in which some of the hydrogen atoms may be substituted by an alkyl group containing 1 to 10 carbon atoms or the terminal methyl group may be substituted by an aryl group.

Examples of the aromatic amido acid compound (b2) used for the present invention include compounds represented by any one of the undermentioned general formulae (6) to (8). Such compounds may also be used as dissolution accelerators.

[Chemical compound 10]

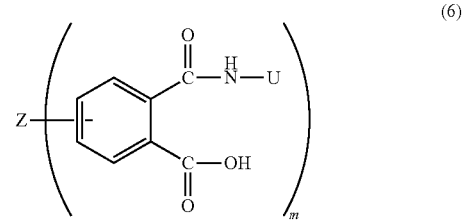

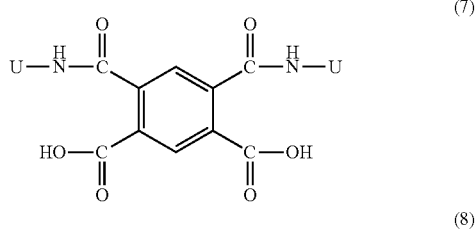

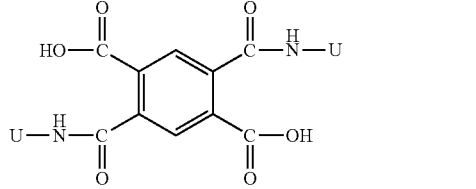

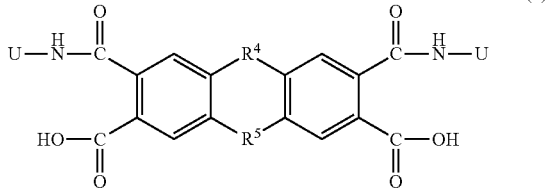

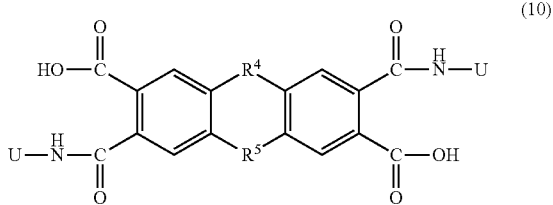

In general formulae (6) to (10), m is an integer of 1 to 4. U is a monovalent organic group that has an alkyl group containing 2 to 20 carbon atoms and bonding directly to the amide nitrogen in general formulae (6) to (10) or a monovalent organic group that has —(YO)$_n$—. Y is an alkylene group containing 1 to 10 carbon atoms, and n is an integer of 1 to 20. When U is an alkyl group, it preferably contains 10 or less, more preferably 6 or less, carbon atoms. In the case where U is a monovalent organic group containing —(YO)$_n$—, Y is preferably a methylene group, an ethylene group, a propylene group, or a butylene group. In the case where Y is a methylene group, n is preferably 2 or more, more preferably 3 or more. It is also preferably 10 or less. In the case where Y is not a methylene group, n is preferably 2 to 10. Furthermore, U may contain any appropriate substituent group and, for example, preferably has an aryl group at a chain end.

In general formulae (6) to (10), Z is a single bond, a hydrogen atom, an alkoxy group, —O—, —SO$_2$—, —C(CF$_3$)$_2$—, —O—R$^1$—O—, —C(=O)—, —C(=O)O—R$^2$—OC(=O)—, —C(=O)NH—R$^3$—NHC(=O)—, or a monovalent to tetravalent hydrocarbon group containing 1 to 20 carbon atoms. R$^1$ to R$^3$ are each a divalent hydrocarbon group containing 1 to 20 carbon atoms, and R$^4$ and R$^5$ are each —C(CH$_3$)$_2$—, —C(CF$_3$)$_2$—, —O— or —S—. From the viewpoint of ensuring an improved solubility, the hydrocarbon group more preferably contains 1 to 10 carbon atoms. The hydrocarbon group may be either saturated or unsaturated. When Z is a single bond, however, m should be 2.

An aromatic amido acid compound (b2) to use for the present invention can be prepared by reacting an anhydride, a dianhydride, a dicarboxylic acid compound, or a tetracarboxylic acid compound with a corresponding primary amine.

Examples of the anhydride include phthalic anhydride. Examples of the dianhydride include those aromatic tetracarboxylic dianhydrides which are mentioned above as good dianhydrides to use to form polyimides. Examples of the dicarboxylic acid include phthalic acid. Examples of the tetracarboxylic acid include those aromatic tetracarboxylic acids which are mentioned above as good tetracarboxylic acids to use to form a polyimide precursor or a polybenzoxazole precursor.

Examples of the primary amine include aliphatic amines such as ethyl amine, propyl amine, butyl amine, pentyl amine, hexyl amine, heptyl amine, octyl amine, nonyl amine, decyl amine, and dodecyl amine, in which some of the hydrogen atoms may be substituted by an alkyl group containing 1 to 10 carbon atoms or the terminal methyl group may be substituted by an aryl group.

For the resin composition according to the present invention, the amido-phenol compound (b1) and/or the aromatic amido acid compound (b2) preferably account for 1 part by mass or more, more preferably 3 parts by mass or more, relative to 100 parts by mass the alkali-soluble resin (a) from the viewpoint of ensuring an improved sensitivity whereas they preferably account for 50 parts by mass or less, more preferably 40 parts by mass or less, from the viewpoint of ensuring an improved heat resistance.

<Photosensitive Compound (c)>

The resin composition according to the present invention preferably contains a photosensitive compound (c) to serve as a photosensitive resin composition. Examples of the photosensitive compound (c) include photo acid generators (c1) and photo-initiators (c2). A photo acid generator (c1) is a compound that generates an acid when exposed to light whereas a photo-initiator (c2) is a compound that undergoes bond cleavage and/or reaction to generate a radical when exposed to light.

The incorporation of the photo acid generator (c1) works to generate an acid in the light-exposed regions so that the light-exposed regions increase in solubility in an aqueous alkali solution, allowing a positive type relief pattern to be formed after the dissolution of the light-exposed regions. The incorporation of an epoxy compound or a thermal crosslinking agent as described later along with the photo acid generator (c1) allows the acid formed in the light-exposed regions to serve for accelerating the crosslinking reaction of the epoxy compound and the thermal crosslinking agent, leading to the formation of a negative type relief pattern as a result of insolubilization of the light-exposed regions. On the other hand, the incorporation of a radical polymerizable compound as described later along with the photo-initiator (c2) allows radical polymerization to progress in the light-exposed regions, leading to the formation of a negative type relief pattern as a result of insolubilization of the light-exposed regions.

Examples of the photo acid generator (c1) include quinone diazide compounds, sulfonium salts, phosphonium salts, diazonium salts, and iodonium salts. It is also preferable that two or more photo acid generators (c1) are contained to provide a photosensitive resin composition with high sensitivity.

Examples of the quinone diazide compounds include a polyhydroxy compound bonded to a sulfonic acid of quinone diazide through ester linkage, a polyamino compound bonded to a sulfonic acid of quinone diazide through sulfonamide linkage, and a polyhydroxypolyamino compound bonded to a sulfonic acid of quinone diazide through ester linkage and/or sulfonamide linkage. It is preferable that 50 mol % or more of the functional groups in these polyhydroxy compounds and polyamino compounds are substituted by quinone diazide.

For the quinone diazide used for the present invention, both 5-naphthoquinone diazide sulfonyl group and 4-naphthoquinone diazide sulfonyl group are used preferably. A 4-naphthoquinone diazide sulfonyl ester compound absorbs light in the i-line range of mercury lamps, and therefore, it is suitable for i-line light exposure. A 5-naphthoquinone diazide sulfonyl ester compound absorbs light in a region including the g-line of mercury lamps, and therefore, it is suitable for g-line light exposure. For the present invention, it is preferable to adopt either a 4-naphthoquinone diazide sulfonyl ester compound or a 5-naphthoquinone diazide sulfonyl ester compound depending on the wavelength of the light used for exposure. Furthermore, it may include a naphthoquinone diazide sulfonyl ester compound that contains both a 4-naphthoquinone diazide sulfonyl group and a 5-naphthoquinone diazide sulfonyl group in one molecule, or may include both a 4-naphthoquinone diazide sulfonyl ester compound and a 5-naphthoquinone diazide sulfonyl ester compound.

A quinone diazide compound as described above can be synthesized through an any appropriate esterification reaction between a compound containing a phenolic hydroxyl group and a quinone diazide sulfonic acid compound. The use of such a quinone diazide compound serves to further improve the resolution, sensitivity, and residual film percentage.

Of the above examples of the photo acid generator (c1), sulfonium salts, phosphonium salts, diazonium salts, and iodonium salts are preferable because they can stabilize moderately the acid component produced by light exposure. The use of a sulfonium salt is particularly preferable. In addition, a sensitization agent etc. may also be added as required.

For the present invention, the photo acid generator (c1) preferably accounts for 0.01 to 50 parts by mass relative to 100 parts by mass of the alkali-soluble resin (a) from the viewpoint of ensuring an increased sensitivity. In particular, the quinone diazide compound preferably accounts for 3 to 40 parts by mass. The sulfonium salts, phosphonium salts, diazonium salts, and iodonium salts preferably account altogether for 0.5 to 20 parts by mass.

Examples of the photo-initiator (c2) include benzyl ketal based photo-initiators, α-hydroxyketone based photo-initiators, α-aminoketone based photo-initiators, acyl phosphine oxide based photo-initiators, oxime ester based photo-initiators, acridine based photo-initiators, titanocene based photo-initiators, benzophenone based photo-initiators, acetophenone based photo-initiators, aromatic keto ester based photo-initiators, and benzoic acid ester based photo-initiators. Two or more photo-initiators (c2) may be contained together. From the viewpoint of ensuring an improved sensitivity, the use of an α-aminoketone based photo-initiator, an acyl phosphine oxide based photo-initiator, or an oxime ester based photo-initiator is more preferable.

Examples of the α-aminoketone based photo-initiator include 2-methyl-1-[4-(methylthio)phenyl]-2-morpholinopropane-1-one, 2-benzyl-2-dimethylamino-1-(4-morpholinophenyl)-butane-1-one, 2-dimethylamino-2-(4-methylbenzyl)-1-(4-morpholinophenyl)-butane-1-one, and 3,6-bis(2-methyl-2-morpholinopropionyl)-9-octyl-9H-carbazole.

Examples of the acyl phosphine oxide based photo-initiator include 2,4,6-trimethylbenzoyl-diphenylphosphine oxide, bis(2,4,6-trimethylbenzoyl)-phenylphosphine oxide, and bis(2,6-dimethoxybenzoyl)-(2,4,4-trimethylpentyl) phosphine oxide.

Examples of the oxime ester based photo-initiator include 1-phenylpropane-1,2-dione-2-(O-ethoxycarbonyl) oxime, 1-phenylbutane-1,2-dione-2-(O-methoxycarbonyl) oxime, 1,3-diphenylpropane-1,2,3-trione-2-(O-ethoxycarbonyl) oxime, 1-[4-(phenylthio)phenyl] octane-1,2-dione-2-(O-benzoyl) oxime, 1-[4-[4-(carboxyphenyl)thio]phenyl] propane-1,2-dione-2-(O-acetyl) oxime, 1-[9-ethyl-6-(2-methylbenzoyl)-9H-carbazole-3-yl] ethanone-1-(O-acetyl) oxime, 1-[9-ethyl-6-[2-methyl-4-[1-(2,2-dimethyl-1,3-dioxolan-4-yl) methyloxy] benzoyl]-9H-carbazole-3-yl] ethanone-1-(O-acetyl) oxime, and 1-(9-ethyl-6-nitro-9H-carbazole-3-yl)-1-[2-methyl-4-(1-methoxypropane-2-yloxy) phenyl] methanone-1-(O-acetyl) oxime.

For the present invention, the photo-initiator (c2) preferably accounts for 0.1 part by mass or more, more preferably 1 part by mass or more, relative to the total quantity of the alkali-soluble resin (a) and the radical polymerizable compound that will be described later, which altogether account for 100 parts by mass, from the viewpoint of ensuring an improved sensitivity. On the other hand, the content is preferably 25 parts by mass or less, more preferably 15 parts by mass or less, from the viewpoint of ensuring an improved resolution and a smaller taper angle.

<Radical Polymerizable Compound>

The resin composition according to the present invention may further contain a radical polymerizable compound.

A radical polymerizable compound is a compound that has a plurality of ethylenically unsaturated double bonds in its molecule. In the light exposure step, radicals generated from the photo-initiator (c2) work to accelerate the radical polymerization of the radical polymerizable compound to cause insolubilization of the light-exposed regions, leading to the formation of a negative type pattern. Furthermore, the incorporation of a radical polymerizable compound serves to accelerate the photo-curing of the light-exposed regions, leading to an improved sensitivity. In addition, the crosslink density after the heat curing step will increase, resulting in a cured film with an improved hardness.

It is preferable for the radical polymerizable compound to be a (meth)acrylic group-containing compound because such a compound will be radically polymerized easily. It is more preferable for the compound to have two or more (meth)acrylic groups in the molecule from the viewpoint of ensuring an improved sensitivity in the light exposure step and producing a cured film with an increased hardness. The radical polymerizable compound preferably has a double bond equivalent of 80 to 400 g/mol from the viewpoint of ensuring an improved sensitivity in the light exposure step and producing a cured film with an increased hardness.

Examples of the radical polymerizable compound include trimethylolpropane tri(meth)acrylate, ditrimethylolpropane tri(meth)acrylate, ditrimethylolpropane tetra(meth)acrylate, pentaerythritol tri(meth)acrylate, pentaerythritol tetra(meth)acrylate, dipentaerythritol penta(meth)acrylate, dipentaerythritol hexa(meth)acrylate, tripentaerythritol hepta(meth)acrylate, tripentaerythritol octa(meth)acrylate, 2,2-bis[4-(3-(meth)acryloxy-2-hydroxypropoxy) phenyl] propane, 1,3,5-tris-((meth)acryloxyethyl) isocyanuric acid, 1,3-bis((meth)acryloxyethyl) isocyanuric acid, 9,9-bis[4-(2-(meth)acryloxyethoxy) phenyl] fluorene, 9,9-bis[4-(3-(meth)acryloxy propoxy) phenyl] fluorene, and 9,9-bis(4-(meth)acryloxyphenyl) fluorene, as well as acid-modified forms thereof, ethylene oxide-modified forms thereof, and propylene oxide-modified forms thereof.

For the present invention, the radical polymerizable compound preferably accounts for 15 parts by mass or more, more preferably 30 parts by mass or more, relative to the total quantity of the alkali-soluble resin (a) and the radical polymerizable compound, which altogether account for 100 parts by mass, from the viewpoint of ensuring an improved sensitivity and a smaller taper angle. On the other hand, the content is preferably 65 parts by mass or less, more preferably 50 parts by mass or less, from the viewpoint of permitting the production of a cured film with further increased heat resistance and ensuring a smaller taper angle.

<Thermal Crosslinking Agent (d)>

The resin composition according to the present invention preferably contains a thermal crosslinking agent (d). A thermal crosslinking agent is a compound that contains, in one molecule, at least two thermally reactive functional groups such as alkoxymethyl groups, methylol groups, epoxy groups, and oxetanyl groups. The incorporation of a thermal crosslinking agent (d) works to form crosslinks between molecules of the alkali-soluble resin (a) or other additional components, thereby serving to produce a heat-cured film with an increased heat resistance, chemical resistance, and hardness. It also realizes the reduction in outgassing from the cured film and the production of an organic EL display device with an increased long-term reliability.

Preferable examples of compounds having at least two alkoxymethyl groups or methylol groups include DML-PC, DML-PEP, DML-OC, DML-OEP, DML-34X, DML-PTBP, DML-PCHP, DML-OCHP, DML-PFP, DML-PSBP, DML-POP, DML-MBOC, DML-MBPC, DML-MTrisPC, DML-BisOC-Z, DML-BisOCHP-Z, DML-BPC, DML-BisOC-P, DMOM-PC, DMOM-PTBP, DMOM-MBPC, TriML-P, TriML-35XL, TML-HQ, TML-BP, TML-pp-BPF, TML-BPE, TML-BPA, TML-BPAF, TML-BPAP, TMOM-BP, TMOM-BPE, TMOM-BPA, TMOM-BPAF, TMOM-BPAP, HML-TPPHBA, HML-TPHAP, HMOM-TPPHBA, and HMOM-TPHAP (trade names, all manufactured by Honshu Chemical Industry Co., Ltd.); and NIKALAC (registered trademark) MX-290, NIKALAC (registered trademark) MX-280, NIKALAC (registered trademark) MX-270, NIKALAC (registered trademark) MX-279, NIKALAC (registered trademark) MW-100LM, and NIKALAC (registered trademark) MX-750LM (all trade names, manufactured by Sanwa Chemical Co., Ltd.).

Preferable examples of compounds having at least two epoxy groups include Epolight (registered trademark) 40E, Epolight (registered trademark) 100E, Epolight (registered trademark) 200E, Epolight (registered trademark) 400E, Epolight (registered trademark) 70P, Epolight (registered trademark) 200P, Epolight (registered trademark) 400P, Epolight (registered trademark) 1500NP, Epolight (registered trademark) 80MF, Epolight (registered trademark) 4000, and Epolight (registered trademark) 3002 (all manufactured by Kyoeisha Chemical Co., Ltd.); Denacol (registered trademark) EX-212L, Denacol (registered trademark) EX-214L, Denacol (registered trademark) EX-216L, and Denacol (registered trademark) EX-850L (all manufactured by Nagase ChemteX Corporation); GAN and GOT (both manufactured by Nippon Kayaku Co., Ltd.); Epikote (registered trademark) 828, Epikote (registered trademark) 1002, Epikote (registered trademark) 1750, Epikote (registered trademark) 1007, YX8100-BH30, E1256, E4250, and E4275 (all manufactured by Japan Epoxy Resins Co., Ltd.); Epicron (registered trademark) EXA-9583 and HP4032 (both manufactured by DIC Corporation); VG3101 (manufactured by Mitsui Chemicals, Inc.); Tepic (registered trademark) S, Tepic (registered trademark) G, and Tepic (registered trademark) P (all manufactured by Nissan Chemical Industries, Ltd.); Denacol (registered trademark) EX-321L (manufactured by Nagase ChemteX Corporation); NC6000 (manufactured by Nippon Kayaku Co., Ltd.); Epotohto (registered trademark) YH-434L (manufactured by Tohto Kasei Co., Ltd.); EPPN502H, NC3000 (manufactured by Nippon Kayaku Co., Ltd.); and Epicron (registered trademark) N695 and HP7200 (both manufactured by DIC Corporation).

Preferable examples of compounds having at least two oxetanyl groups include Eternacoll EHO, Eternacoll OXBP, Eternacoll OXTP, and Eternacoll OXMA (all manufactured by Ube Industries, Ltd.), and oxetanized phenol novolac.

Two or more of these thermal crosslinking agents may be used in combination.

The thermal crosslinking agent preferably accounts for 1 part by mass or more and 30 parts by mass or less relative to the total quantity of the resin composition excluding the solvents, which accounts for 100 parts by mass. If accounting for 1 part by mass or more, the thermal crosslinking agent can serve to produce a calcined or cured film with a higher chemical resistance and hardness. If accounting for 30 parts by mass or less, the thermal crosslinking agent can serve to ensure the reduction in outgassing from the cured film, the production of an organic EL display device with an increased long-term reliability, and the preparation of a resin composition with an increased storage stability.

<Cyclic Amide, Cyclic Urea, and Derivatives Thereof>

The resin composition to use for the cured film according to the present invention preferably contains at least one compound selected from the group consisting of cyclic amides, cyclic ureas, and derivatives thereof. It is considered that such one or more compounds selected from the group consisting of cyclic amides, cyclic ureas, and derivatives thereof will remain in the cured film that results from the curing of the resin composition according to the present invention and work as a quencher for acidic gases to serve to prevent a decrease in light emission luminance or shrinkage of pixels and provide an organic EL display device having an improved long-term reliability.

Such one or more compounds selected from the group consisting of cyclic amides, cyclic ureas, and derivatives thereof preferably have structures as represented by general formula (17) given below.

[Chemical compound 11]

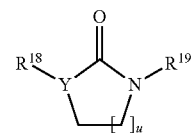

(17)

In general formula (17), u denotes an integer of 1 to 4 and Y denotes CH or a nitrogen atom. $R^{25}$ and $R^{26}$ each independently represent a hydrogen atom or an organic group containing 1 to 20 carbon atoms.

Such one or more compounds (e) selected from the group consisting of cyclic amides, cyclic ureas, and derivatives thereof each preferably have a boiling point of 210° C. or more to ensure easy persistence in the cured film. The boiling point is preferably 400° C. or less from the viewpoint of reducing uneven coating. If the boiling point cannot be measured under atmospheric pressure, a measured value can be converted to an estimated boiling point under atmospheric pressure using a boiling point conversion table.

Specific examples of the cyclic amides, cyclic ureas, and derivatives thereof include 2-pyrrolidone, N-methyl-2-pyrrolidone (NMP), N-ethyl-2-pyrrolidone, N-propyl-2-pyrrolidone, N-isopropyl-2-pyrrolidone, N-butyl-2-pyrrolidone, N-(t-butyl)-2-pyrrolidone, N-pentyl-2-pyrrolidone, N-cyclohexyl-2-pyrrolidone, N-methoxypropyl-2-pyrrolidone, N-ethoxyethyl-2-pyrrolidone, N-methoxybutyl-2-pyrrolidone, N-(2-hydroxyethyl)-2-pyrrolidone, N-phenyl-2-pyrrolidone, N-vinyl-2-pyrrolidone, N, N'-dimethyl propylene urea, 2-imidazolidinone, 1,3-dimethyl-2-imidazolidinone, 2-piperidone, and ε-caprolactam. Two or more of these may be contained together. Of these, N-cyclohexyl-2-pyrrolidone (boiling point 154° C. at 0.933 kPa, converted boiling point at atmospheric pressure 305° C.), N-(2-hydroxyethyl)-2-pyrrolidone (boiling point 175° C. at 1.333 kPa, converted boiling point at atmospheric pressure 313° C.) are preferable because they are high enough in boiling point to remain more easily after heat treatment.

It is preferable for such one or more compounds selected from the group consisting of cyclic amides, cyclic ureas, and derivatives thereof to account altogether for 0.1 part by mass or more, more preferably 1 part by mass or more, relative to 100 parts by mass of the alkali-soluble resin (a), from the viewpoint of producing an organic EL display device with an increased long-term reliability. In the case of a photosensitive resin composition, on the other hand, it is preferable for such one or more compounds selected from the group consisting of cyclic amides, cyclic ureas, and derivatives thereof to account altogether for 15 parts by mass or less, more preferably 10 parts by mass or less, relative to 100 parts by mass of the alkali-soluble resin (a), from the viewpoint of ensuring a further increased sensitivity.

<Organic Solvent>

The resin composition according to the present invention may contain an organic solvent. The incorporation of an organic solvent allows the resin composition to be in a varnish-like state, ensuring improved coatability.

Useful examples of the organic solvent include, for example, polar aprotic solvents such as γ-butyrolactone; ethers such as ethylene glycol monomethyl ether, ethylene glycol monoethyl ether, ethylene glycol mono-n-propyl ether, ethylene glycol mono-n-butyl ether, diethylene glycol monomethyl ether, diethylene glycol monoethyl ether, diethylene glycol mono-n-propyl ether, diethylene glycol mono-n-butyl ether, triethylene glycol monomethyl ether, triethylene glycol monoethyl ether, propylene glycol monomethyl ether, propylene glycol monoethyl ether, propylene glycol mono-n-propyl ether, propylene glycol mono-n-butyl ether, dipropylene glycol monomethyl ether, dipropylene glycol monoethyl ether, dipropylene glycol mono-n-propyl ether, dipropylene glycol mono-n-butyl ether, tripropylene glycol monomethyl ether, tripropylene glycol monoethyl ether, tetrahydrofuran, and dioxane; ketones such as acetone, methyl ethyl ketone, diisobutyl ketone, cyclohexanone, 2-heptanone, 3-heptanone, and diacetone alcohol; esters such as ethylene glycol monomethyl ether acetate, ethylene glycol monoethyl ether acetate, diethylene glycol monomethyl ether acetate, diethylene glycol monoethyl ether acetate, propylene glycol monomethyl ether acetate, propylene glycol monoethyl ether acetate, and ethyl lactate; other esters such as ethyl 2-hydroxy-2-methylpropionate, methyl 3-methoxypropionate, ethyl 3-methoxypropionate, methyl 3-ethoxypropionate, ethyl 3-ethoxypropionate, ethyl ethoxyacetate, ethyl hydroxyacetate, methyl 2-hydroxy-3-methylbutanoate, 3-methoxybutyl acetate, 3-methyl-3-methoxybutyl acetate, 3-methyl-3-methoxybutylpropionate, ethyl acetate, n-propyl acetate, i-propyl acetate, n-butyl acetate, i-butyl acetate, n-pentyl formate, i-pentyl acetate, n-butyl propionate, ethyl butyrate, n-propyl butyrate, i-propyl butyrate, n-butyl butyrate, methyl pyruvate, ethyl pyruvate, n-propyl pyruvate, methyl acetoacetate, ethyl acetoacetate, and ethyl 2-oxobutanoate; aromatic hydrocarbons such as toluene and xylene; and amide compounds such as N-methyl pyrrolidone, N,N-dimethyl formamide, and N,N-dimethyl acetamide. Two or more of these may be contained together.

There are no specific limitations on the content of the organic solvent, but it preferably accounts for 100 to 3,000 parts by mass, more preferably 150 to 2,000 parts by mass, relative to the total quantity of the resin composition excluding the solvents, which accounts for 100 parts by mass. Furthermore, although some components of the organic solvent may have boiling points of 180° C. or more, it is preferable for the solvent components having boiling points of 180° C. or more to account for 20 parts by mass or less, more preferably 10 parts by mass or less, relative to the total quantity of the organic solvent. If the solvent components having boiling points of 180° C. or more account for 20 parts by mass or less, it will be possible to reduce the outgassing from the heat-cured film, thereby resulting in an organic EL display device with an increased long-term reliability.

<Coloring Agent>

The resin composition according to the present invention may further contain a coloring agent.

A coloring agent is a compound that absorbs light in a specific wavelength range and in particular, it is a compound that acts to color a material by absorbing light in the visible light wavelength range (380 to 780 nm). The incorporation of the coloring agent serves to obtain a colored film from a resin composition and impart coloring capability to the film prepared from a resin composition to allow the light penetrating the film of the resin composition or the light reflected by the film of the resin composition to have a desired color. It also serves to impart light blocking capability since light in the specific wavelength range is absorbed by the coloring agent and removed from the light penetrating the film of the resin composition or the light reflected by the film of the resin composition.

The coloring agent may be a compound that absorbs light in a visible light wavelength range for coloring in white, red, orange, yellow, green, blue, or violet. Two or more of coloring agent components may be used in combination to ensure an improved toning capability since the color coordinates of the light penetrating the film of the resin composition or the light reflected by the film of the resin composition can be adjusted as desired.

The coloring agent is preferably a pigment and/or a dye. The coloring agent may be either a black one or non-black one.

A black coloring agent is a compound that acts to color a material black by absorbing light in the visible light wavelength range and may be either a pigment or a dye. If containing a black coloring agent, the film of a resin composition turns black to improve the light blocking capability since the light penetrating the film of the resin composition or reflected by the film of the resin composition is blocked efficiently. Thus, such a film can be used suitably in such components as light blocking films for black matrices of color filters, black column spacers of liquid crystal display devices, etc., and other components that require increased contrast realized by depression of external light reflection.

From the viewpoint of light blocking capability, the black coloring agent is preferably a compound that can color a material black by absorbing light over the entire visible light wavelength range. It is also preferable to use a mixture of two or more compounds selected from those for white, red, orange, yellow, green, blue, and violet. An appropriate combination of two or more of these can serve to color a material pseudo-black to ensure an improved light blocking capability.

The black agent preferably contain a black pigment, black dye, and/or a combination of two or more dyes, and more preferably contains a black pigment from the viewpoint of light blocking capability.

A non-black coloring agent is a compound that serves to color a material by absorbing light in a visible light wavelength range. Examples thereof include coloring agents that serve for coloring in non-black colors including white, red, orange, yellow, green, blue, and violet, as described above. The incorporation of a non-black coloring agent serves to allow the film of the resin composition to have light blocking capability, coloring capability, and toning capability.

The non-black coloring agent is preferably a non-black pigment and/or a non-black dye, more preferably a non-black pigment from the viewpoint of light blocking capability, and heat resistance or weather resistance.

The coloring agent preferably accounts for 5 part by mass or more, more preferably 15 parts by mass or more, relative to the total quantity of the resin composition excluding the solvents, which accounts for 100 parts by mass. If accounting for 5 parts by mass or more, the coloring agent can ensure an improved light blocking capability, coloring capability, and toning capability. On the other hand, the coloring agent preferably accounts for 70 parts by mass or less, more preferably 60 parts by mass or less. If accounting for 70 parts by mass or less, the coloring agent can ensure a further improved sensitivity.

<Adhesion Promoter>

The resin composition according to the present invention may contain an adhesion promoter. Examples of the adhesion promoter include silane coupling agents such as vinyl trimethoxysilane, vinyl triethoxysilane, epoxy cyclohexylethyl trimethoxysilane, 3-glycidoxypropyl trimethoxysilane, 3-glycidoxypropyl triethoxysilane, p-styryl trimethoxysilane, 3-aminopropyl trimethoxysilane, 3-aminopropyl triethoxysilane, and N-phenyl-3-aminopropyl trimethoxysilane, and others such as titanium chelating agents, aluminum chelating agents, and those compound resulting from reaction between an aromatic amine compound and an alkoxy group-containing silicon compound. Two or more of these may be contained together. If such an adhesion promoter is contained, the resin film can come in stronger contact with the substrate material such as silicon wafer, ITO, $SiO_2$, and nitride silicon during the development step. It also serves to improve the resistance to oxygen plasma and UV ozone processing used for cleaning etc.

The adhesion promoter preferably accounts for 0.1 to 10 parts by mass relative to the total quantity of the resin composition excluding the solvents, which accounts for 100 parts by mass.

<Surfactant>

The resin composition according to the present invention may contain a surfactant as required to ensure improved wetting of the substrate. Examples of the surfactant include silicone based surfactants such as SH series, SD series, and ST series manufactured by Toray Dow Corning Silicone Co., Ltd., BYK series manufactured by BYK Japan KK, KP series manufactured by Shin-Etsu Silicones, Disfoam series manufactured by NOF Corporation, and TSF series manufactured by Toshiba Silicone Co., Ltd.; fluorochemical surfactants such as Megafac (registered trademark) series manufactured by Dainippon Ink and Chemicals Inc., Fluorad series manufactured by Sumitomo 3M Limited, Surflon (registered trademark) series and Asahi Guard (registered trademark) series manufactured by Asahi Glass Co., Ltd., EF series manufactured by Shin-Akita Kasei Co., Ltd., and PolyFox series manufactured by OMNOVA Solutions Inc.; and acrylic and/or methacrylic polymer based surfactants such as Polyflow series manufactured by Kyoeisha Chemical Co., Ltd. and Disparlon (registered trademark) series manufactured by Kusumoto Chemicals Ltd.

The surfactant preferably accounts for 0.001 to 1 part by mass relative to the total quantity of the resin composition excluding the solvents, which accounts for 100 parts by mass.

<Inorganic Particles>

The resin composition according to the present invention may contain inorganic particles. Specifically, the inorganic particles are of materials such as, for example, silicon oxide, titanium oxide, barium titanate, alumina, and talc. It is preferable for the inorganic particles to have a primary particle diameter of 100 nm or less, more preferably 60 nm or less. The inorganic particles preferably account for 5 to 90 parts by mass relative to the total quantity of the resin composition excluding the solvents, which accounts for 100 parts by mass.

<Thermal Acid Generator and Thermal Base Generator>

The resin composition according to the present invention may contain a thermal acid generator or thermal base generator unless it impedes the production of an organic EL display apparatus with a long term reliability. When heated, a thermal acid generator and a thermal base generator generate an acid and base, respectively, that accelerate the crosslinking reaction of the thermal crosslinking agent (d) and stimulate the cyclization of unclosed imide ring structures and oxazole ring structures if such structures exist in the resin of component (a) to ensure the production of a cured film with further improved mechanical characteristics. They also serve to accelerate the cyclodehydration reaction of the amido-phenol compound (b1) and the aromatic amido acid compound (b2) in the curing step to allow a cured film with a low water absorptivity to be obtained at a low heat-curing temperature of 250° C. or below.

The thermal acid generator or thermal base generator to use for the present invention preferably has a heat decomposition starting temperature of 50° C. to 270° C., more preferably 250° C. or less. In addition, it is preferable to adopt one that does not generate an acid or base in the first drying step (for prebaking at about 70° C. to 140° C.) following the coating of a substrate with the resin composition according to the present invention and generates an acid or base in the final heating step (for curing at about 100° C. to 400° C.) following the light exposure and developments steps for patterning. This serves to prevent a decrease in sensitivity during development.

The acid generated by the thermal acid generator used for the present invention is preferably a strong acid, and preferable examples thereof include aryl sulfonic acids such as p-toluene sulfonic acid and benzene sulfonic acid; alkyl sulfonic acids such as methane sulfonic acid, ethane sulfonic acid, propane sulfonic acid, and butane sulfonic acid; and haloalkyl sulfonic acids such as trifluoromethyl sulfonic acid. These are used in the form of salts such as onium salt or covalent compounds such as imide sulfonate. Two or more of these may be contained together.

Examples of preferable thermal base generators for the present invention include guanidine trichloroacetate, methylguanidine trichloroacetate, potassium trichloroacetate, guanidine phenylsulfonylacetate, guanidine p-chlorophenylsulfonylacetate, guanidine p-methanesulfonylphenylsulfonylacetate, potassium phenylpropiolate, guanidine phenylpropiolate, cesium phenylpropiolate, guanidine p-chlorophenylpropiolate, guanidine p-phenylene-bis-phenylpropiolate, tetramethylammonium phenylsulfonylacetate, and tetramethylammonium phenylpropiolate. Two or more of these may be contained together.

The thermal acid generator or the thermal base generator preferably accounts for 0.01 part by mass or more, more preferably 0.1 part by mass or more, relative to the total quantity of the resin composition excluding the solvents, which accounts for 100 parts by mass. The incorporation of 0.01 part by mass or more of the thermal acid generator or the thermal base generator serves to accelerate the crosslinking reaction and the cyclization of unclosed ring structures in the resin to ensure the production of a cured film with further improved mechanical characteristic and chemical resistance. The content is preferably 5 parts by mass or less, more preferably 2 parts by mass or less, from the viewpoint of obtaining an organic EL display apparatus with a long term reliability.

<Production Method for Resin Composition>

Described below is the production method for the resin composition according to the present invention. For example, a resin composition can be obtained by dissolving the aforementioned alkali-soluble resin (a), amido-phenol compound (b1), and/or aromatic amido acid compound (b2), along with a photosensitive compound (c), thermal cross-linking agent (d), radical polymerizable compound, cyclic amide, cyclic urea, derivative of either, organic solvent, coloring agent, adhesion promoter, surfactant, inorganic particles, thermal acid generator, thermal base generator, etc., as required. This dissolution can be carried out by stirring, heating, etc. When heating is performed, an appropriate heating temperature is adopted in a range, commonly from room temperature to 80° C., where the performance of the resin composition is not impaired. There are no specific limitations on the order of dissolving these components, and for example, the compound with the lowest solubility may be dissolved first followed by others in the order of solubility. Otherwise, the dissolution of those components that are likely to form bubbles when dissolved by stirring, such as surfactants and some adhesion promoters, may be postponed to the other components so that the dissolution of the latter will not be hindered by bubble formation.

The resulting resin composition is preferably filtrated through a filter to remove dust and particles. Filters with a pore size of, for example, 0.5 μm, 0.2 μm, 0.1 μm, 0.07 μm, 0.05 μm, or 0.02 μm are available, though there are no specific limitations on the size. The filter to use may be of such a material as polypropylene (PP), polyethylene (PE), nylon (NY), and polytetrafluoroethylene (PTFE), of which polyethylene and nylon are preferable.

<Resin Sheet>

A resin sheet to use for the present invention is produced from the aforementioned resin composition.

Such a resin sheet can be prepared by, for example, spreading the aforementioned resin composition over a strippable base material such as polyethylene terephthalate to form a coating film of the resin composition and drying it. A protective film may be added on top of it.

Available coating methods include, for example, the spin coating method, slit coating method, dip coating method, spray coating method, and printing method. Of these, the use of the slit coating method is preferable because of requiring only a small amount of a coating liquid to achieve sufficient coating and being advantageous for cost reduction. For example, the slit coating method requires only one-fifth to one-tenth of the amount of a coating liquid required by the spin coating method. An appropriate slit nozzle designed for coating may be selected from various products provided by different manufacturers including Linear Coater manufactured by Dainippon Screen Mfg. Co., Ltd., Spinless manufactured by Tokyo Ohka Kogyo Co., Ltd., TS Coater manufactured by Toray Engineering Co., Ltd., Table Coater manufactured by Chugai Ro Co., Ltd., CS series and CL series manufactured by Tokyo Electron Ltd., In-line Slit Coater manufactured by Cermatronics Boeki Co., Ltd., and Head Coater HC series manufactured by Hirata Corporation. Such coating is performed commonly in the speed range of 10 mm/sec to 400 mm/sec. Depending on the solid content and the viscosity of the resin composition, coating is commonly performed to form a film with a thickness of 0.1 to 10 μm, preferably 0.3 to 5 μm, after being dried.

Before the coating step, the base to be coated with the resin composition may be pre-treated with an adhesion promoter as described above. As a typical pre-treatment procedure, an adhesion promoter may be dissolved in a solvent such as isopropanol, ethanol, methanol, water, tetrahydrofuran, propylene glycol monomethyl ether acetate, propylene glycol monomethyl ether, ethyl lactate, and diethyl adipate to prepare a 0.5 to 20 wt % solution, which is then used to treat the surface of the base. Such treatment of the surface of the base may be carried out by an appropriate technique such as spin coating, slit die coating, bar coating, dip coating, spray coating, and steam treatment.

After the coating, reduced pressure drying may be performed as required. Commonly, the coating film is subjected to reduced pressure drying together with the substrate that carries it. For example, the substrate with the coating film formed on it is placed on proxy pins arranged in a vacuum chamber, followed by reducing the pressure in the vacuum chamber to carry out reduced pressure drying. In this step, a large volume of air, if existing in the space between the substrate and the ceiling of the vacuum chamber, can move during reduced pressure drying to cause drying marks. To prevent this, it is preferable to adjust the height of the proxy pins to decrease the distance between the substrate and the ceiling of the vacuum chamber. The distance between the substrate and the ceiling of the vacuum chamber is preferably 2 to 20 mm, more preferably 2 to 10 mm.

Depending on the volume of the vacuum chamber, the capacity of the vacuum pump, the diameter of the pipe connecting the chamber to the pump, etc., it is preferable for the rate of reduced pressure drying to be set, for example, in such a manner that the pressure in the vacuum chamber containing no coated substrate is reduced to 40 Pa in 60 seconds. Commonly, the reduced pressure drying time is set to about 30 to 100 seconds, and the final pressure in the vacuum chamber that contains the coated substrate is 100 Pa or less at the end of the reduced pressure drying step. A final pressure maintained at or below 100 Pa allows the coating film surface to be in a less sticky, dry state, serving to prevent surface contamination and particle formation from taking place during the subsequent substrate conveyance step.

Commonly, the coating film is dried by heating after the coating step or the reduced pressure drying step. This step is referred to as pre-baking. Drying is carried out by using a hot plate, oven, infrared ray, or the like. When using a hot plate, the coating film is put directly on the plate or held on jigs such as proxy pins fixed on the plate while heating. Various proxy pins of different materials are available including metals such as aluminum and stainless steel and synthetic resins such as polyimide resin and Teflon (registered trademark). Any types of proxy pins may be adopted if they have heat resistance. Depending on the size of the substrate, type of the coating film, and purpose of the heating, it is preferable for the height of the proxy pins to be in the range of about 0.1 to 10 mm. The optimum heating temperature and heating period depend on the type and purpose of the coating film, but heating is performed preferably at a heating temperature in the range of 50 to 180° C. for a heating period of 1 minute to several hours.

In the case where the resin sheet is photosensitive, it is possible to form a pattern. For example, light exposure is performed by applying an actinic ray to a photosensitive resin sheet through a mask having an intended pattern, and then the pattern is created by developing the sheet.

Actinic rays available for the light exposure step include ultraviolet ray, visible light, electron beam, and X-ray. For the invention, it is preferable to use the i-line (365 nm), h-line (405 nm), or g-line (436 nm) of mercury lamps. If the sheet is positively photosensitive, the exposed regions dissolves in a developer. If the film is negatively photosensitive, the exposed regions harden and become insoluble in a developer.

After the exposure step, a developer is used to remove the exposed regions of the positive sheet or unexposed regions of the negative sheet to form an intended pattern. Preferable developers include an aqueous solution of alkaline compounds such as tetramethyl ammonium hydroxide, diethanol amine, diethyl aminoethanol, sodium hydroxide, potassium hydroxide, sodium carbonate, potassium carbonate, triethyl amine, diethyl amine, methyl amine, dimethyl amine, dimethylaminoethyl acetate, dimethylaminoethanol, dimethylaminoethyl methacrylate, cyclohexyl amine, ethylene diamine, and hexamethylene diamine. Such aqueous alkali solutions may also contain polar solvents such as N-methyl-2-pyrolidone, N,N-dimethyl formamide, N,N-dimethyl acetamide, dimethyl sulfoxide, γ-butyrolactone, and dimethyl acrylamide; alcohols such as methanol, ethanol and isopropanol; esters such as ethyl lactate and propylene glycol monomethyl ether acetate; and ketones such as cyclopentanone, cyclohexanone, isobutyl ketone, and methyl isobutyl ketone; which may be added singly or as a combination of two or more thereof. Available development techniques include spraying, paddling, immersion, and ultrasonic vibration.

The pattern formed by development is preferably rinsed with distilled water. The distilled water to use for the rinsing may contain an alcohol such as ethanol and isopropyl alcohol, an ester such as ethyl lactate and propylene glycol monomethyl ether acetate, or the like.

<Cured Film>

The cured film according to the present invention can be obtained by curing the resin sheet or the resin composition.

The cured film according to the present invention contains an alkali-soluble resin (a), a benzoxazole compound as represented by any one of general formulae (11) to (13), and/or an imide compound as represented by any one of general formulae (14) to (16) given below. The benzoxazole compounds represented by general formulae (11) to (13) can result from dehydration cyclization of the amido-phenol compounds represented by general formulae (3) to (5), respectively, and the imide compounds represented by general formulae (14) to (16) can result from dehydration cyclization of the aromatic amido acid compounds represented by general formulae (6) to (10), respectively.

[Chemical compound 12]

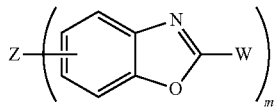
(11)

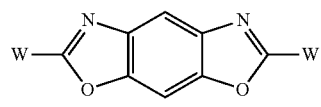
(12)

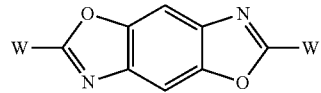
(13)

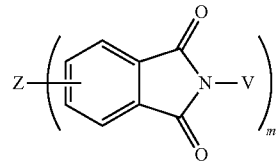
(14)

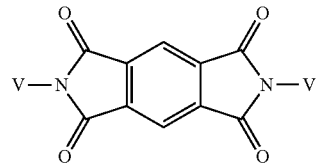
(15)

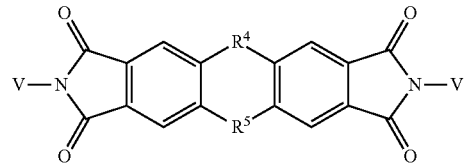
(16)

In general formulae (11) to (13), W is a monovalent organic group that has an alkyl group containing 2 to 20 carbon atoms and bonding directly to a carbon atom in the oxazole ring in general formulae (11) to (13) or a monovalent organic group that has —(YO)$_n$—. In general formulae (14) to (16), V is a monovalent organic group that has an alkyl group containing 2 to 20 carbon atoms and bonding directly to a nitrogen atom in the imide ring in general formulae (14) to (16) or a monovalent organic group that has —(YO)$_n$—. Here, m is an integer of 1 to 4; Y is an alkylene group containing 1 to 10 carbon atoms; and n is an integer of 1 to 20. Z is a single bond, a hydrogen atom, an alkoxy group, —O—, —SO$_2$—, —C(CF$_3$)$_2$—, —O—R$^1$—O—, —C(=O)—, —C(=O)O—R$^2$—OC(=O)—, —C(=O)NH—R$^3$—NHC(=O)—, or a monovalent to tetravalent hydrocarbon group containing 1 to 20 carbon atoms. R$^1$ to R$^3$ are each a divalent hydrocarbon group containing 1 to 20 carbon atoms, and R$^4$ and R$^5$ are each —C(CH$_3$)$_2$—, —C(CF$_3$)$_2$—, —O— or —S—. When Z is a single bond, however, m should be 2.

As the cured film contains an alkali-soluble resin (a), a benzoxazole compound as represented by any one of general formulae (11) to (13), and/or an imide compound as represented by any one of general formulae (14) to (16), it is possible to obtain a cured film with a low water absorption rate.

The cured film can contain one compound selected from the group consisting of cyclic amides, cyclic ureas, and derivatives thereof. The total content of the cyclic amides, cyclic ureas, and derivatives thereof is 0.005 mass % or more and 5 mass % or less in 100 mass % of the cured film.

By heat-curing the resin composition or resin sheet, components with low heat resistance can be removed to ensure an improved heat resistance and chemical resistance. In particular, when the resin composition or resin sheet according to the present invention contains a polyimide precursor, polybenzoxazole precursor, a copolymer thereof, or a copolymer of one thereof with a polyimide, imide rings or oxazole rings will be formed by heat-curing to ensure an improved heat resistance and chemical resistance. If a thermal crosslinking agent (d) is contained, furthermore, the heat-curing step works to promote the thermal crosslinking reaction and accordingly, the heat resistance and chemical resistance will be improved.

From the viewpoint of reducing the outgassing from the cured film, the heat-curing temperature is preferably 300° C. or more and more preferably 350° C. or more. On the other hand, from the viewpoint of obtaining a cured film with a high ductility, it is preferably 500° C. or less and more preferably 450° C. or less. In this temperature range, the temperature may be raised stepwise or continuously. From the viewpoint of reducing the outgassing, the heat-curing time is preferably 30 minutes or more. On the other hand, from the viewpoint of obtaining a cured film with a higher ductility, it is preferably 3 hours or less. For example, heat treatment may be performed at 150° C., and 250° C. for 30 minutes each, or heat treatment may be performed by raising the temperature linearly from room temperature to 300° C. over a 2-hour period.

The resin composition, resin sheet, and cured film according to the present invention can be applied suitably to surface protection layer and interlaminar insulation layer of semiconductor devices, insulation layer of organic electroluminescence (hereinafter abbreviated as EL) devices, planarization layer for the substrate of thin film transistors (hereinafter abbreviated as TFT) to drive displaying components that incorporate organic EL devices, wiring-protecting insulation layer of circuit boards, on-chip microlens for solid imaging devices, and planarization layers for various display and solid imaging devices. For example, they are highly suitable as material for surface protection layers and interlaminar insulation layers of MRAMs, which are low in heat resistance, polymer ferroelectric RAMs (PFRAMs), which are promising as next generation memory component, and phase change memories (phase change RAM (PCRAM), Ovonics Unified Memory (OUM)). They also can be applied to insulation layers in various display apparatuses that contain a first electrode formed on a substrate and a second electrode disposed opposite to the first electrode, such as those display apparatuses that incorporate LCDs, ECDs, ELDs, organic electroluminescent devices (organic electroluminescent apparatuses), etc. They will be described below focusing on organic EL display apparatuses, semiconductor equipment, and semiconductor electronic components.

<Organic EL Display Apparatus>

The organic EL display apparatus according to the present invention includes a drive circuit, planarization layer, first electrode, insulation layer, luminescence layer, and second electrode mounted on a substrate, of which the planarization layer and/or insulation layer are formed from the cured film according to the present invention. Organic EL luminescence materials are generally liable to degradation caused by moisture and susceptible to adverse influences such as a decrease in the ratio of the area of the luminescent region to that of the luminescent pixels, but the cured film according to the present invention is low enough in water absorption rate to maintain stable drive performance and luminescence characteristics. An active matrix type display apparatus, for example, is composed mainly of a substrate of glass, various plastics, or the like, a TFT, wiring located on the side of the TFT, connected to the TFT, and disposed on the substrate, a planarization layer disposed on top of it so as to cover surface irregularities, and a display device disposed on the planarization layer. The display device and wiring are connected to each other through a contact hole provided in the planarization layer.

FIG. 1 gives a cross section of a typical TFT substrate. Bottom gate type or top gate type TFTs (thin film transistors) 1 are disposed along lines on a substrate 6, and an insulation layer 3 is disposed so as to cover these TFTs 1. Wires 2 connected to the TFTs 1 are provided on this insulation layer 3. On top of the insulation layer 3, furthermore, a planarization layer 4 is provided to embed the wires 2. The planarization layer 4 contains contact holes 7 that reach the wires 2. An ITO (transparent electrode) 5 is located on the planarization layer 4 and connected to the wires 2 through the contact holes 7. Here, the ITO 5 works as an electrode of the display device (for example, organic EL device). In addition, an insulation layer 8 is provided so as to cover the margin of the ITO 5. This organic EL device can work as either a top emission type one that emits luminescence from the opposite side to the substrate 6 or a bottom emission type one that emits luminescence from the substrate 6 side. Thus, an active matrix type organic EL display device in which each organic EL device is connected to a TFT 1 to drive it is obtained.

As described above, the insulation layer 3, planarization layer 4, and/or insulation layer 8 can be produced by a step for forming a photosensitive resin film of the resin composition or resin sheet according to the present invention, a step for exposing the photosensitive resin film to light, a step for developing the light-exposed photosensitive resin film, and a step for heat-treating the developed photosensitive resin film. An organic EL display apparatus can be produced by carrying out a production procedure that includes these steps.

<Semiconductor Electronic Component and Semiconductor Equipment>

The semiconductor electronic component and semiconductor equipment according to the present invention each include an electrode, metal wiring, interlaminar insulation layer, and/or surface protection layer disposed on a substrate, of which the interlaminar insulation layer and/or surface protection layer are made of the cured film according to the present invention. Having good mechanical characteristics, the cured film according to the present invention in the mounted state can work to relax the stress caused by sealant resin and accordingly serves to provide highly reliable semiconductor equipment by reducing the damage to the low-k layer (low dielectric constant layer).

Figure 2:
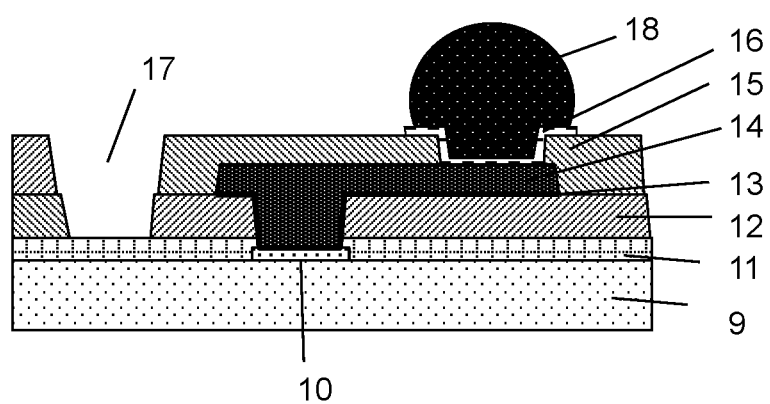
FIG. 2 is an enlarged cross-sectional view of a typical pat member of semiconductor equipment with a bump.
Figure 3:
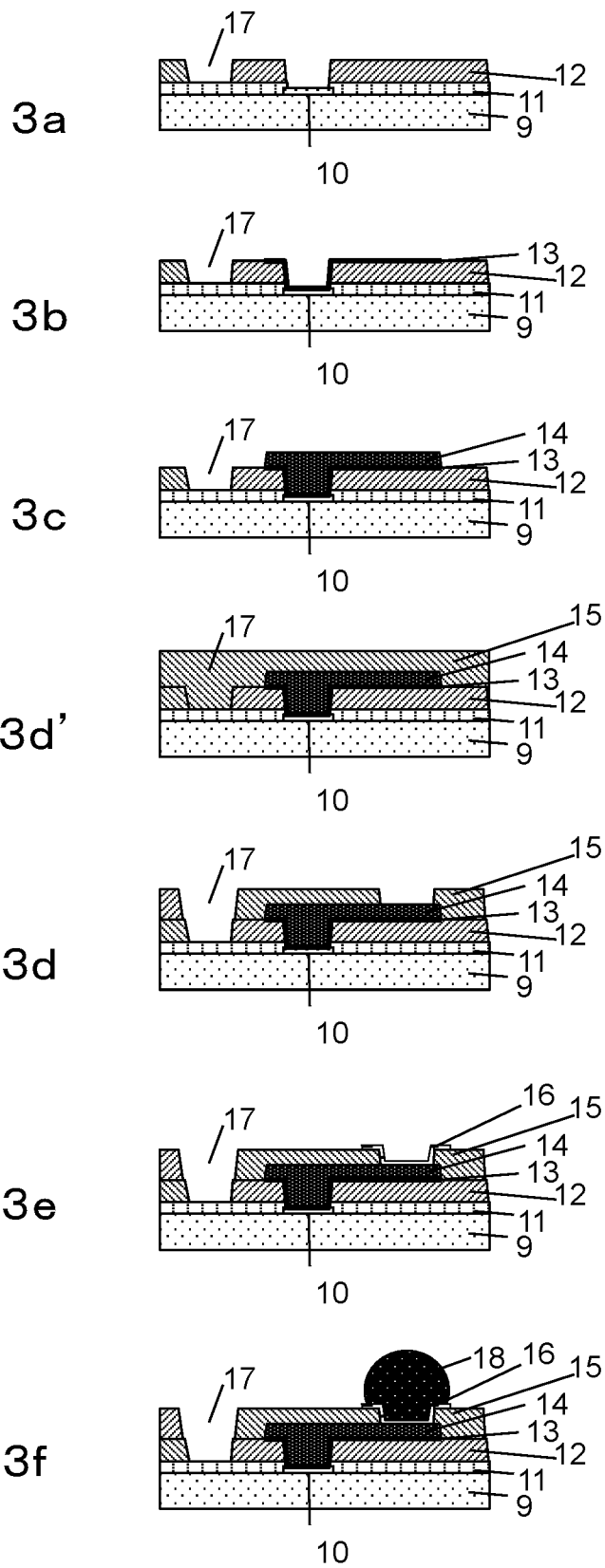
FIG. 3(a) to (f) are schematic diagrams illustrating a typical method for producing semiconductor equipment with a bump.

FIG. 2 is an enlarged cross-sectional view of a typical pad member of semiconductor equipment with a bump. A passivation layer 11 having an input/output Al pad 10 and a via hole is disposed on a silicon wafer 9. In addition, there are an insulation layer 12 located on the passivation layer 11, a metal layer 13 of Cr, Ti, etc., connected to the Al pad 10, and a metal wiring 14 which is formed of Al, Cu, etc., by electrolytic plating etc. The plurality of pads are insulated from each other by etching the metal layer 13 located on the periphery of the solder bump 18. A barrier metal 16 and a solder bump 18 are disposed on each insulated pad.

Next, the production method for semiconductor equipment is described with reference to drawings. FIGS. 3a to 3f illustrate a typical method for producing semiconductor equipment with a bump. In the step in FIG. 3a, the resin composition according to the present invention is spread over a silicon wafer 9 that has an Al pad 10 and a passivation layer 11 formed thereon and subjected to photolithographic processing to provide a patterned insulation layer 12. Then, in the step in FIG. 3b, a metal layer 13 is formed by sputtering. In the step in FIG. 3c, a metal wiring 14 is formed on the metal layer 13 by plating. Subsequently, the resin composition according to the present invention is spread in the step in FIG. 3d and subjected to photolithographic processing in the step in FIG. 3d to produce a patterned insulation layer 15. Meanwhile, the resin composition in the insulation layer 15 is thickened in the scribe line 17.

Additional wiring (so-called rewiring) may be formed on top of the insulation layer 15. To form a multi-layered structure containing two or more wiring layers, this step is performed repeatedly to produce a multi-layered wiring structure containing two or more rewiring layers that are separated from each other by interlaminar insulation layers of the cured film according to the present invention. There are no limitations on the upper limit to the number of layers in the multi-layered wiring structure, but generally structures composed of 10 or less layers are used. Then, a barrier metal 16 is formed in the step in FIG. 3e and a solder bump 18 is formed in the step in FIG. 3f. Finally, the structure is diced along the scribe line 17 into chips to provide semiconductor equipment with a bump.

EXAMPLES

The present invention will be illustrated below in greater detail with reference to Examples, but it should be understood that the invention is not construed as being limited thereto. The evaluations of the resin composition samples prepared in Example are carried out using the following methods.

(1) Sensitivity

The varnish sample prepared in each Example and Comparative example was spread over an 8-inch silicon wafer by the spin coating technique using a coating and developing apparatus (Mark-7, manufactured by Tokyo Electron Ltd.) and baked on a hot plate (SCW-636, manufactured by Dainippon Screen Mfg. Co., Ltd.) at 120° C. for 3 minutes to produce a prebaked film with a film thickness of 3.0 µm. Here, the film thickness was measured using a Lambda Ace STM-602, manufactured by Dainippon Screen Mfg. Co., Ltd., under the condition of a refractive index of 1.63. Subsequently, using a light exposure machine (NSR-2005i9C i-line stepper, manufactured by Nicon Corporation), it was exposed to light through a mask having a 10 µm contact hole pattern to an exposure of 100 to 1,200 mJ/cm² in steps of 50 mJ/cm². After the light exposure step, using the Mark-7 developing apparatus, it was developed with an aqueous solution containing 2.38 wt % tetramethyl ammonium (hereinafter referred to as TMAH, manufactured by Tama Chemicals Co., Ltd.) used as developer until the film loss reached 0.5 µm, followed by rinsing with distilled water and drying by shaking off water to produce a pattern.

The resulting pattern was observed at a magnification of 20 times using a FDP microscope MX61 (manufactured by Olympus Corporation) to measure the opening diameter of the contact hole. The minimum exposure energy required until the opening diameter of the contact hole reached 10 µm was determined to represent the sensitivity.

(2) Water Absorption Rate

The varnish sample prepared in each Example and Comparative example was spread on a silicon wafer by spin coating using a spin coater (MS-A100, manufactured by Mikasa Co., Ltd.) at an appropriate rotating speed and prebaked on a hot plate (SCW-636, manufactured by Dainippon Screen Mfg. Co., Ltd.) at 120° C. for 120 seconds to produce a prebaked film with a thickness of about 10.0 µm. Here, the film thickness was measured using a Lambda Ace STM-602, manufactured by Dainippon Screen Mfg. Co., Ltd., under the condition of a refractive index of 1.63. The resulting prebaked film was heated at an oxygen concentration of 20 ppm or less in a high temperature inert gas oven (INH-9CD-S, manufactured by Koyo Thermo Systems Co., Ltd.) by raising the temperature to 250° C. at a heating rate of 5° C./min, followed by performing heat treatment at 250° C. for 1 hour to produce a cured film of the resin composition. Then, the resulting cured film was immersed in a 45 mass % hydrogen fluoride solution to remove the film from the silicon wafer. The cured film obtained was washed sufficiently with pure water and then dried in an oven at 60° C. for 5 hours to provide a film. The resulting film was dried at 50° C. for 24 hours and then immersed in pure water maintained at 23° C. Subsequently, after measuring its weight in a nitrogen atmosphere at room temperature using a thermogravimetric analysis apparatus (TGA-50, manufactured by Shimadzu Corporation), it was heated from room temperature to 100° C. and maintained at 100° C. for 30 minutes, followed by measuring its weight and calculating the water absorption rate based on the decrease from the weight of the film at room temperature to that at 100° C.

(3) 5% Weight Loss Temperature

A film was prepared by the same procedure as for item (2) and 10 mg thereof was put in a thermogravimetric analysis apparatus (TGA-50, manufactured by Shimadzu Corporation), heated in a nitrogen atmosphere from room temperature to 100° C., and further maintained at 100° C. for 30 minutes, followed by measuring the weight. Subsequently, it was heated up to 400° C. at a heating rate of 10° C./minute while measuring the weight to determine the temperature at which the weight decreased by 5% from the weight measured after the heating at 100° C. for 30 minutes.

Listed below are thermal crosslinking agents (d-1) and (d-2), phenol compounds (e-1) to (e-3), and a thermal acid generator (f-1) used in Examples and Comparative examples.

[Chemical compound 13]

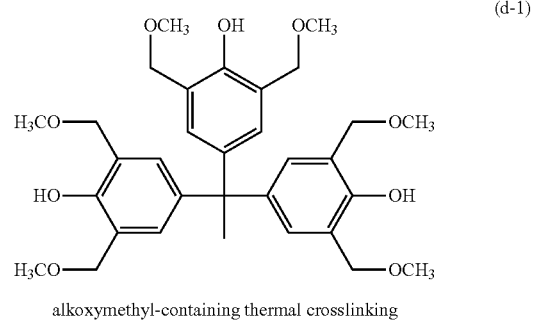

alkoxymethyl-containing thermal crosslinking (d-1)

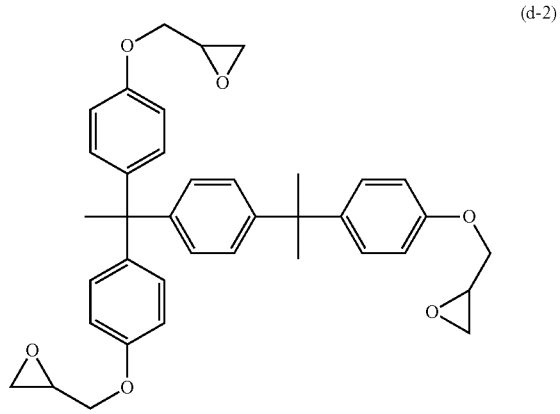

VG-3101L (d-2)

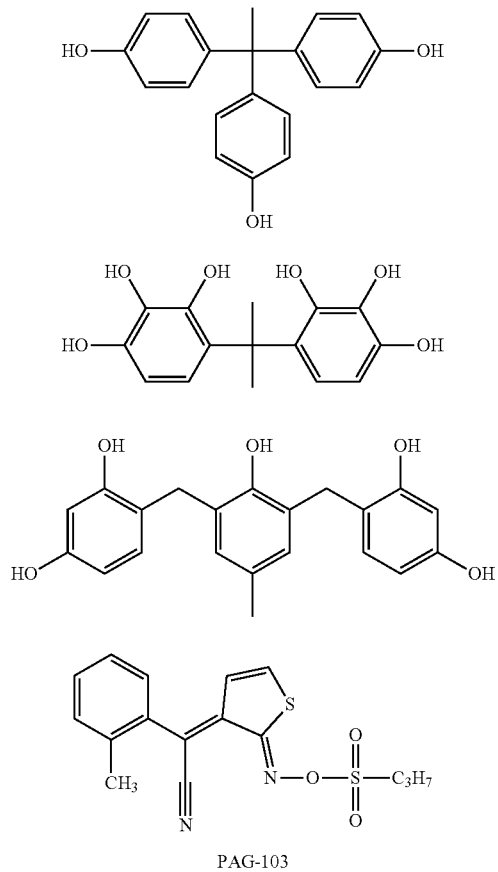

(e-1)

(e-2)

(e-3)

(f-1)

PAG-103

Synthesis Example 1

Synthesis of Hydroxyl-Containing Diamine Compound (α)

First, 18.3 g (0.05 mole) of 2,2-bis(3-amino-4-hydroxyphenyl) hexafluoropropane (hereinafter referred to as BAHF) was dissolved in 100 mL of acetone and 17.4 g (0.3 mole) of propylene oxide, and cooled to −15° C. Then, a solution of 20.4 g (0.11 mole) of 3-nitrobenzoyl chloride dissolved in 100 mL of acetone was added dropwise. After the end of dropping, the solution was allowed to react at −15° C. for 4 hours, followed by allowing it to return to room temperature. The resulting white solid precipitate was separated out by filtration and vacuum dried at 50° C.

A 30 g portion of the resulting white solid material was put in a 300 mL stainless steel autoclave and dispersed in 250 mL of methyl cellosolve, followed by adding 2 g of 5% palladium-carbon. Then, a balloon was used to introduce hydrogen to cause a reduction reaction at room temperature. About 2 hours later, the reaction was finished after checking that the balloon would deflate no more. After the end of the reaction, the solution was filtrated to remove the palladium compound used as catalyst and concentrated with a rotary evaporator to provide hydroxyl-containing diamine compound (α) as represented by the formula given below.

[Chemical compound 14]

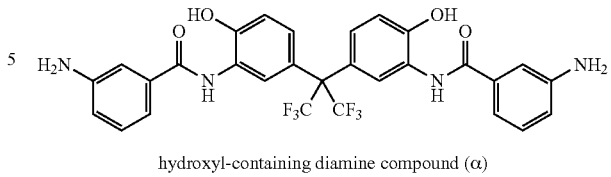

hydroxyl-containing diamine compound (α)

Synthesis Example 2

Synthesis of Alkali-Soluble Resin (a-1)

In a dry nitrogen flow, 31.0 g (0.10 mole) of 3,3',4,4'-diphenyl ether tetracarboxylic dianhydride (hereinafter referred to as ODPA) was dissolved in 500 g of N-methyl-2-pyrrolidone (NMP). Here, 45.35 g (0.075 mole) of the hydroxyl group-containing diamine compound prepared in Synthesis example 1 and 1.24 g (0.005 mole) of 1,3-bis(3-aminopropyl) tetramethyl disiloxane were added together with 50 g of NMP, followed by performing reaction at 20° C. for 1 hour and additional reaction at 50° C. for 2 hours. Then, 4.36 g (0.04 mole) of 4-aminophenol, used as end-capping agent, was added together with 5 g of NMP, followed by performing reaction at 50° C. for 2 hours. Subsequently, a solution prepared by diluting 28.6 g (0.24 mole) of N,N-dimethylformamide dimethylacetal with 50 g of NMP was added dropwise over 10 minutes. After the dropping, stirring was performed at 50° C. for 3 hours. After the stirring, the solution was cooled to room temperature and then the solution was poured into 3 L of water to provide a white precipitate. This precipitate was collected by filtration, rinsed with water 3 times, and dried in a vacuum drying machine at 80° C. for 24 hours to provide a polyimide precursor (a-1) which was an alkali-soluble resin.

Synthesis Example 3

Synthesis of Alkali-Soluble Resin (a-2)

In a dried nitrogen flow, 29.3 g (0.08 mole) of BAHF, 1.24 g (0.005 mole) of 1,3-bis(3-aminopropyl) tetramethyl disiloxane, and 3.27 g (0.03 mole) of 3-aminophenol, which was used as end capping agent, were dissolved in 150 g N-methyl-2-pyrrolidone (NMP). To this solution, 31.0 g (0.1 mole) of ODPA was added together with 50 g of NMP, stirred at 20° C. for 1 hour, and additionally stirred at 50° C. for 4 hours. Subsequently, 15 g of xylene was added and stirred at 150° C. for 5 hours while distilling water in an azeotropic state with xylene. After the stirring, the solution was poured in 3 L of water and the resulting white precipitate was collected. This precipitate was collected by filtration, rinsed with water 3 times, and dried in a vacuum drying machine at 80° C. for 24 hours to provide a polyimide (a-2) which was an alkali-soluble resin.

Synthesis Example 4

Synthesis of Alkali-Soluble Resin (a-3)

In a dry nitrogen flow, 18.3 g (0.05 mole) of BAHF was dissolved in 50 g of NMP and 26.4 g (0.3 mole) of glycidyl methyl ether, and the temperature of the solution was decreased to −15° C. Then, a solution prepared by dissolving 7.4 g (0.025 mole) of diphenyl ether dicarboxylic acid dichloride (manufactured by Nihon Nohyaku Co., Ltd.) and 5.1 g (0.025 mole) of isophthalic acid chloride (manufactured by Tokyo Chemical Industry Co., Ltd.) in 25 g of γ-butyrolactone (GBL) was added dropwise while maintaining the internal temperature at or below 0° C. After the completion of the dropping, stirring was continued at −15° C. for 6 hours. After the end of the reaction, the solution was poured in 3 L of water containing 10 wt % methanol and white precipitate was collected. This precipitate was collected by filtration, rinsed with water 3 times, and dried in a vacuum drying machine at 80° C. for 24 hours to provide a polybenzoxazole precursor (a-3) which was an alkali-soluble resin.

Synthesis Example 5

Synthesis of Alkali-Soluble Resin (a-4)

In a 500 ml flask, 5 g of 2,2'-azobis(isobutyronitrile), 5 g of t-dodecane thiol, and 150 g of propylene glycol monomethyl ether acetate (hereinafter abbreviated as PGMEA) were fed. Subsequently, 30 g of methacrylic acid, 35 g of benzyl methacrylate, and 35 g of tricyclo[5.2.1.0$^{2,6}$]decane-8-yl methacrylate were added and stirred for a while at room temperature, followed by filling the flask with nitrogen and stirring while heating at 70° C. for 5 hours. Then, 15 g of glycidyl methacrylate, 1 g of dimethylbenzyl amine, and 0.2 g of p-methoxyphenol were add to the resulting solution, followed by stirring while heating at 90° C. for 4 hours to provide an acrylic resin solution (a-4) which was an alkali-soluble resin. The resulting acrylic resin solution had a solid content of 43 wt %.

Synthesis Example 6

Synthesis of Alkali-Soluble Resin (a-5)

In a dry nitrogen flow, 70.2 g (0.65 mole) of m-cresol, 37.8 g (0.35 mole) of p-cresol, 75.5 g (formaldehyde 0.93 mole) of a 37 wt % aqueous formaldehyde solution, 0.63 g (0.005 mole) of oxalic dihydrate, and 264 g of methyl isobutyl ketone were fed, immersed in an oil bath, and subjected to condensation polymerization reaction for 7 hours while refluxing the reaction liquid. Subsequently, the temperature of the oil bath was increased by heating for 3 hours, and then the pressure in the flask was reduced to 40 to 67 hPa to remove volatile matters, followed by cooling the dissolved resin to room temperature and adding GBL to prepare a novolac resin (a-5) which was an alkali-soluble resin having a nonvolatile content adjusted to 50%. The resulting novolac resin (a-5) had a weight average molecular weight of 7,000.

Synthesis Example 7

Synthesis of Amido-Phenol Compound (b1-1)

First, 10.9 g (0.1 mole) of 2-aminophenol was dissolved in 200 mL of tetrahydrofuran (THF) and 30.4 g (0.3 mole) of triethyl amine. Then, a solution of 19.1 g (0.1 mole) of decanoyl chloride dissolved in 100 mL of THF was added dropwise at a temperature of −10° C. or below. After the end of the dropwise addition, the reaction was continued at room temperature for 4 hours. Subsequently, a 1% hydrochloric acid solution was added, and the reaction solution was extracted with ethyl acetate to remove the solvent, followed by vacuum drying the resulting solid at 50° C. to provide an amido-phenol compound (b1-1) as represented by the formula given below.

[Chemical compound 15]

(b1-1)

Synthesis Example 8

Synthesis of Amido-Phenol Compound (b1-2)

Except for using 36.3 g (0.1 mole) of bis(3-amino-4-hydroxyphenyl) hexafluoropropane (BAHF) instead of 10.9 g (0.1 mole) of 2-aminophenol, and using 38.1 g (0.2 mole), instead of 19.1 g (0.1 mole), of decanoyl chloride, the same procedure as in Synthesis example 7 was carried out to produce an amido-phenol compound (b1-2) as represented by the formula given below.

[Chemical compound 16]

(b1-2)

Synthesis Example 9

Synthesis of Amido-Phenol Compound (b1-3)

Except for using 21.3 g (0.2 mole) of butyryl chloride instead of 38.1 g (0.2 mole) of decanoyl chloride, the same procedure as in Synthesis example 8 was carried out to produce an amido-phenol compound (b1-3) as represented by the formula given below.

[Chemical compound 17]

(b1-3)

Synthesis Example 10

Synthesis of Amido-Phenol Compound (b1-4)

Except for using 33.7 g (0.2 mole) of 3-phenylpropionyl chloride instead of 38.1 g (0.2 mole) of decanoyl chloride, the same procedure as in Synthesis example 8 was carried out to produce an amido-phenol compound (b1-4) as represented by the formula given below.

[Chemical compound 18]

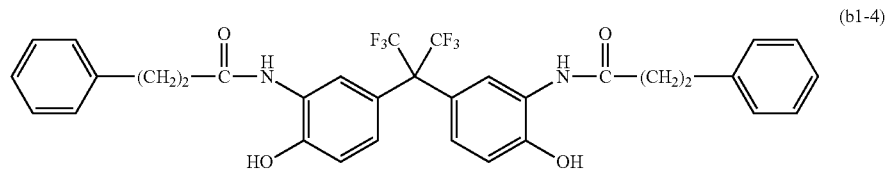

(b1-4)

Synthesis Example 11

Synthesis of Amido-Phenol Compound (b1-5)

Except for using 14.0 g (0.1 mole) of 2,5-dihydroxy-p-phenylene diamine instead of 10.9 g (0.1 mole) of 2-aminophenol and using 38.1 g (0.2 mole), instead of 19.1 g (0.1 mole), of decanoyl chloride, the same procedure as in Synthesis example 7 was carried out to produce an amido-phenol compound (b1-5) as represented by the formula given below.

[Chemical compound 19]

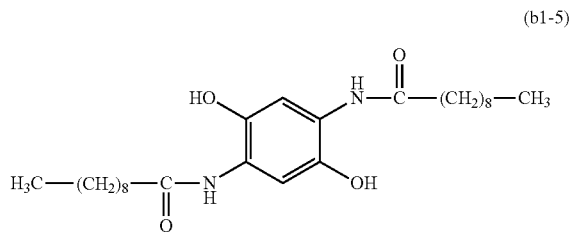

(b1-5)

Synthesis Example 12

Synthesis of Amido-Phenol Compound (b'-6)

Except for using 28.1 g (0.2 mole) of benzoyl chloride instead of 38.1 g (0.2 mole) of decanoyl chloride, the same procedure as in Synthesis example 8 was carried out to produce an amido-phenol compound (b'-6) as represented by the formula given below.

[Chemical compound 20]

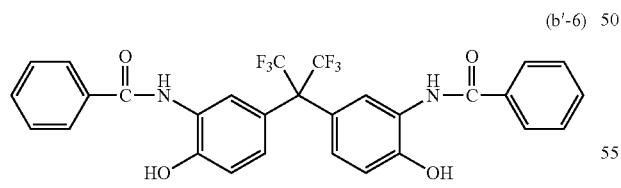

(b'-6)

Synthesis Example 13

Synthesis of Amido-Phenol Compound (b'-7)

Except for using 10.9 g (0.1 mole) of 3-aminophenol instead of 10.9 g (0.1 mole) of 2-aminophenol, the same procedure as in Synthesis example 7 was carried out to produce an amido-phenol compound (b'-7) as represented by the formula given below.

[Chemical compound 21]

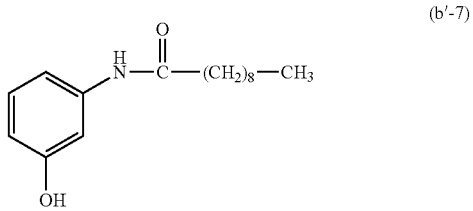

(b'-7)

Synthesis Example 14

Synthesis of Quinone Diazide Compound (c1-1)

In a dry nitrogen flow, 21.22 g (0.05 mole) of TrisP-PA (trade name, manufactured by Honshu Chemical Industry Co., Ltd.) and 36.27 g (0.135 moles) of 5-naphthoquinonediazide sulfonyl acid chloride were dissolved in 450 g of 1,4-dioxane and maintained at room temperature. To this solution, a mixture of 15.18 g of triethyl amine with 50 g of 1,4-dioxane was added dropwise while maintaining the system below 35° C. After the dropping, stirring was performed at 30° C. for 2 hours. The triethylamine salt was filtered and the filtrate was poured in water. Then, the precipitate deposited was collected by filtration. The resulting precipitate was dried in a vacuum drying machine to provide a quinone diazide compound (c1-1) as represented by the formula given below.

[Chemical compound 22]

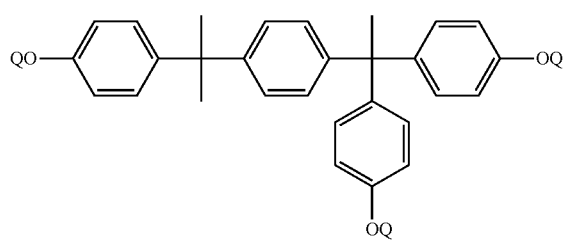

(C-1)

quinone diazide compound

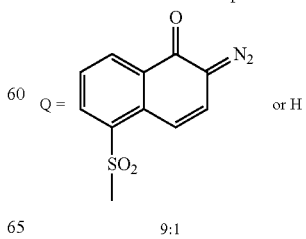

9:1

Synthesis Example 15

Synthesis of Quinone Diazide Compound (c1-2)

In a dry nitrogen flow, 21.22 g (0.05 mole) of TrisP-PA (trade name, manufactured by Honshu Chemical Industry Co., Ltd.) and 36.27 g (0.135 moles) of 4-naphthoquinonediazide sulfonyl acid chloride were dissolved in 450 g of 1,4-dioxane and maintained at room temperature. To this solution, a mixture of 15.18 g of triethyl amine with 50 g of 1,4-dioxane was added dropwise while maintaining the system below 35° C. After the dropping, stirring was performed at 30° C. for 2 hours. The triethylamine salt was filtered and the filtrate was poured in water. Then, the precipitate deposited was collected by filtration. The resulting precipitate was dried in a vacuum drying machine to provide a quinone diazide compound (c1-2) as represented by the formula given below.

[Chemical compound 23]

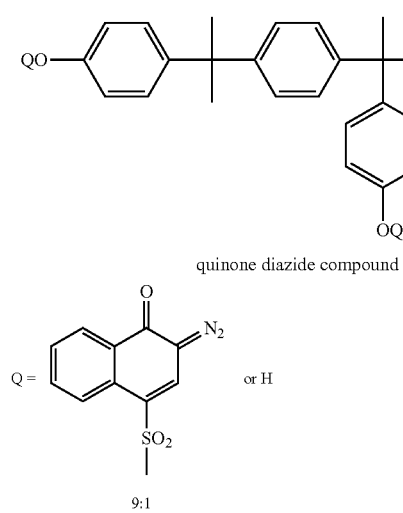

quinone diazide compound

9:1

Synthesis Example 16

Synthesis of Quinone Diazide Compound (c1-3)

In a dry nitrogen flow, 28.83 g (0.05 mole) of TekP-4HBPA (trade name, manufactured by Honshu Chemical Industry Co., Ltd.) and 13.43 g (0.125 moles) of 5-naphthoquinonediazide sulfonyl acid chloride were dissolved in 450 g of 1,4-dioxane and maintained at room temperature. To this solution, a mixture of 15.18 g of triethyl amine with 50 g of 1,4-dioxane was added dropwise while maintaining the system below 35° C. After the dropping, stirring was performed at 30° C. for 2 hours. The triethylamine salt was filtered and the filtrate was poured in water. Then, the precipitate deposited was collected by filtration. The resulting precipitate was dried in a vacuum drying machine to provide a quinone diazide compound (c1-3) as represented by the formula given below.

[Chemical compound 24]

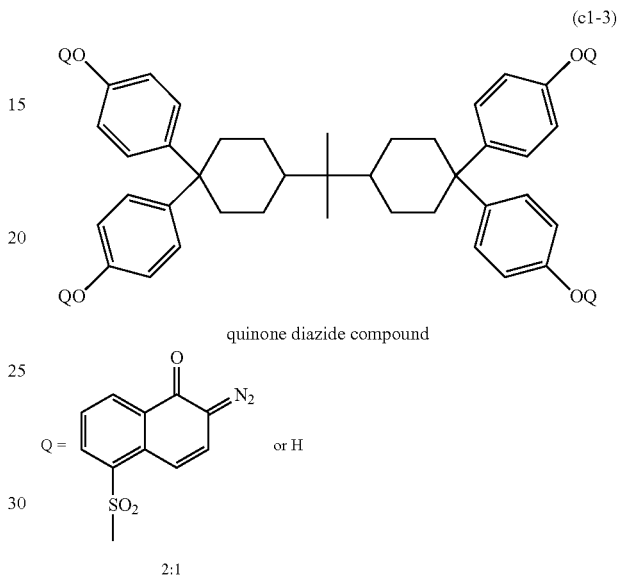

quinone diazide compound

2:1

Example 1

First, 10 g of the resin (a-1), 2.0 g of the amido-phenol compound (b1-1), 2.0 g of the quinone diazide compound (c1-1), and 1.0 g of the crosslinking agent (d-1) were added to 30 g of GBL to prepare a varnish A of a positive type photosensitive resin composition. The resulting varnish A was examined as described above to determine its sensitivity, water absorption rate, and 5% weight loss temperature. Evaluation results are given in Table 1.

Examples 2 to 16 and Comparative Examples 1 to 8

Except for using the components listed in Table 1, the same procedure as in Example 1 was carried out to prepare varnishes B to W. The varnish samples obtained were examined as in Example 1 to determine their sensitivity, water absorption rate, and 5% weight loss temperature. Evaluation results are given in Tables 1 and 2.

TABLE 1

| | Resin composition | Alkali-soluble resin | Phenol compound | Photosensitive compound | Thermal crosslinking agent | Solvent | Other | Sensitivity (mJ/m²) | Water absorption rate (%) | 5% weight loss temperature (° C.) |
|---|---|---|---|---|---|---|---|---|---|---|
| Example 1 | A | a-1 10.0 g | b1-1 1.5 g | c1-1 2.0 g | d-1 1.0 g | GBL 30 g | — — | 140 | 0.7 | 330 |
| Example 2 | B | a-1 10.0 g | b1-2 1.5 g | c1-1 2.0 g | — — | GBL 30 g | — — | 130 | 0.8 | 325 |

TABLE 1-continued

|  | Resin composition | Alkali-soluble resin | Phenol compound | Photosensitive compound | Thermal crosslinking agent | Solvent | Other | Sensitivity (mJ/m²) | Water absorption rate (%) | 5% weight loss temperature (° C.) |
|---|---|---|---|---|---|---|---|---|---|---|
| Example 3 | C | a-1 10.0 g | b1-3 1.5 g | c1-1 2.0 g | — — | GBL 30 g | — — | 135 | 0.8 | 335 |
| Example 4 | D | a-1 10.0 g | b1-1 1.5 g | c1-1 2.0 g | — — | GBL 30 g | — — | 140 | 0.7 | 320 |
| Example 5 | E | a-1 10.0 g | b1-4 1.5 g | c1-1 2.0 g | — — | GBL 30 g | — — | 135 | 0.8 | 340 |
| Example 6 | F | a-1 10.0 g | b1-5 1.5 g | c1-1 2.0 g | — — | GBL 30 g | — — | 125 | 0.8 | 325 |
| Example 7 | G | a-1 10.0 g | b1-2 1.5 g | c1-2 2.0 g | — — | GBL 30 g | — — | 125 | 0.8 | 320 |
| Example 8 | H | a-2 10.0 g | b1-2 1.5 g | c1-1 2.0 g | — — | GBL 30 g | — — | 150 | 0.8 | 330 |
| Example 9 | I | a-2 10.0 g | b1-2 1.5 g | c1-3 2.0 g | — — | GBL 30 g | — — | 145 | 0.8 | 335 |
| Example 10 | J | a-2 10.0 g | b1-5 1.5 g | c1-1 2.0 g | — — | GBL 30 g | — — | 145 | 0.8 | 330 |
| Example 11 | K | a-2 10.0 g | b1-5 1.5 g | c1-1 2.0 g | d-2 0.5 g | GBL 30 g | — — | 150 | 0.8 | 340 |
| Example 12 | L | a-3 10.0 g | b1-2 1.5 g | c1-1 2.0 g | — — | GBL 30 g | — — | 135 | 0.8 | 320 |
| Example 13 | M | a-3 10.0 g | b1-2 1.5 g | c1-3 2.0 g | — — | GBL 30 g | — — | 130 | 0.8 | 325 |
| Example 14 | N | a-4 10.0 g | b1-2 1.5 g | c1-1 2.0 g | — — | GBL 30 g | — — | 120 | 0.6 | 295 |
| Example 15 | O | a-5 10.0 g | b1-2 1.5 g | c1-1 2.0 g | — — | GBL 30 g | — — | 110 | 1.0 | 300 |
| Example 16 | X | a-1 10.0 g | b1-2 1.5 g | c1-1 2.0 g | — — | GBL 30 g | f-1 0.5 g | 130 | 0.7 | 320 |

TABLE 2

|  | Resin composition | Alkali-soluble resin | Phenol compound | Photosensitive compound | Thermal crosslinking agent | Solvent | Other | Sensitivity (mJ/m²) | Water absorption rate (%) | 5% weight loss temperature (° C.) |
|---|---|---|---|---|---|---|---|---|---|---|
| Comparative example 1 | P | a-1 10.0 g | e-1 1.0 g | c1-1 2.0 g | — — | GBL 30 g | — — | 120 | 1.3 | 325 |
| Comparative example 2 | Q | a-1 10.0 g | — — | c1-1 2.0 g | d-1 1.0 g | GBL 30 g | — — | 200 | 0.8 | 330 |
| Comparative example 3 | R | a-1 10.0 g | b'-6 1.5 g | c1-1 2.0 g | — — | GBL 30 g | — — | 140 | 1.2 | 345 |
| Comparative example 4 | S | a-2 10.0 g | b'-6/e-2 1.5 g/1.0 g | c1-1 2.0 g | — — | GBL 30 g | — — | 145 | 1.4 | 330 |
| Comparative example 5 | T | a-2 10.0 g | e-3 1.0 g | c1-3 2.0 g | d-2 0.5 g | GBL 30 g | — — | 135 | 1.5 | 330 |
| Comparative example 6 | U | a-3 10.0 g | — — | c1-1 2.0 g | — — | GBL 30 g | — — | 210 | 0.7 | 330 |
| Comparative example 7 | V | a-3 10.0 g | e-1 1.0 g | c1-1 2.0 g | — — | GBL 30 g | — — | 135 | 1.3 | 325 |
| Comparative example 8 | W | a-1 10.0 g | b'-7 2.0 g | c1-1 2.0 g | — — | GBL 30 g | — — | 140 | 1.3 | 320 |

EXPLANATION OF NUMERALS

1: TFT (thin film transistor)
2: wiring
3: insulation layer
4: planarization layer
5: ITO (transparent electrode)
6: substrate
7: contact hole
8: insulation layer
9: silicon wafer
10: Al pad
11: passivation layer
12: insulation layer
13: metal layer
14: metal wiring
15: insulation layer
16: barrier metal
17: scribe line
18: solder bump

The invention claimed is:

1. A resin composition comprising:
(a) an alkali-soluble resin;
(b1) an amido-phenol compound containing a phenolic hydroxyl group in which a monovalent group as represented by the undermentioned general formula (1) is located at a position ortho to the hydroxyl group; and (c) a photosensitive compound:

(1)

wherein in general formula (1),
X is a monovalent organic group having an alkyl group that contains 2 to 20 carbon atoms and bonds directly to the carbonyl carbon in general formula (1) or a monovalent organic group that has —(YO)$_n$—;
Y is an alkylene group containing 1 to 10 carbon atoms; and
n is an integer of 1 to 20.

2. A resin composition as set forth in claim 1, wherein the amido-phenol compound of (1) is represented by any one of general formulae (3) to (5):

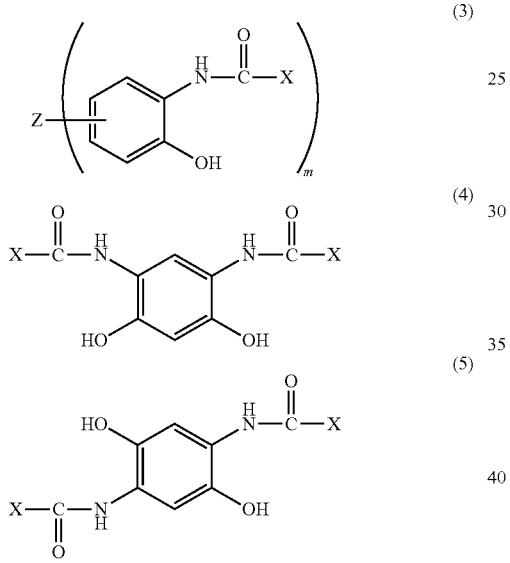

wherein in general formulae (3) to (5),
m is an integer of 1 to 4;
X is a monovalent organic group that has an alkyl group containing 2 to 20 carbon atoms and bonding directly to the carbonyl carbon in general formulae (3) to (5) or a monovalent organic group that has —(YO)$_n$—;
Y is an alkylene group containing 1 to 10 carbon atoms;
n is an integer of 1 to 20;
Z is a single bond, a hydrogen atom, an alkoxy group, —O—, —SO$_2$—, —C(CF$_3$)$_2$—, —O—R$^1$—O—, —C(=O)—, —C(=O)O—R$^2$—OC(=O)—, —C(=O)NH—R$^3$—NHC(=O)—, or a monovalent to tetravalent hydrocarbon group containing 1 to 20 carbon atoms; and
R$^1$ to R$^3$ are each a divalent hydrocarbon group containing 1 to 20 carbon atoms;
m being 2 when Z is a single bond.

3. A resin composition as set forth in claim 1, wherein the alkali-soluble resin of (a) contains polyimide, polybenzoxazole, polyamide-imide, a precursor of any thereof, and/or a copolymer thereof.

4. A resin composition as set forth in claim 1, further comprising: (d) a thermal crosslinking agent.

5. An organic EL display apparatus comprising a drive circuit, a planarization layer, a first electrode, an insulation layer, a luminescence layer, and a second electrode disposed on a substrate, the planarization layer and/or the insulation layer being formed from a cured film produced by curing a resin composition as set forth in claim 1.

6. A semiconductor electronic component comprising an electrode, a metal wiring, an interlaminar insulation layer, and/or a surface protection layer disposed on a substrate, the interlaminar insulation layer and/or the surface protection layer being formed of a cured film produced by curing a resin composition as set forth in claim 1.

7. Semiconductor equipment comprising an electrode, a metal wiring, an interlaminar insulation layer, and/or a surface protection layer disposed on a substrate, the interlaminar insulation layer and/or the surface protection layer being formed of a cured film produced by curing a resin composition as set forth in claim 1.

8. A production method for an organic EL display apparatus comprising a step for producing a photosensitive resin film formed of a resin composition as set forth in claim 1, a step for exposing the photosensitive resin film to light, a step for developing the light-exposed photosensitive resin film, and a step for heat-treating the developed photosensitive resin film.

9. A cured film comprising an alkali-soluble resin (a), and a benzoxazole compound as represented by any one of general formulae (11) to (13) given below:

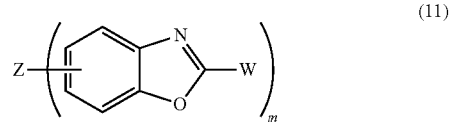
(11)

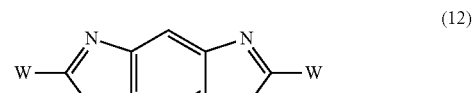
(12)

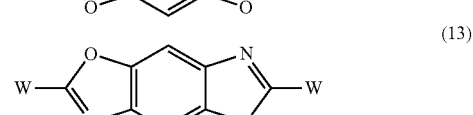
(13)

wherein in general formulae (11) to (13),
W is a monovalent organic group that has an alkyl group containing 2 to 20 carbon atoms and bonding directly to a carbon atom in the oxazole ring in general formulae (11) to (13) or a monovalent organic group that has —(YO)$_n$—;
m is an integer of 1 to 4;
Y is an alkylene group containing 1 to 10 carbon atoms;
n is an integer of 1 to 20;
Z is a single bond, a hydrogen atom, an alkoxy group, —O—, —SO$_2$—, —C(CF$_3$)$_2$—, —O—R$^1$—O—, —C(=O)—, —C(=O)O—R$^2$—OC(=O)—, —C(=O)NH—R$^3$—NHC(=O)—, or a monovalent to tetravalent hydrocarbon group containing 1 to 20 carbon atoms; and
R$^1$ to R$^3$ are each a divalent hydrocarbon group containing 1 to 20 carbon atoms;
m being 2 when Z is a single bond.

* * * * *